US009168306B2

(12) United States Patent
Badea et al.

(10) Patent No.: US 9,168,306 B2
(45) Date of Patent: Oct. 27, 2015

(54) DRUG DELIVERY AGENTS COMPRISING CYCLODEXTRIN COVALENTLY LINKED TO A GEMINI SURFACTANT, AND PHARMACEUTICAL COMPOSITIONS COMPRISING THE SAME

(75) Inventors: Ildiko Badea, Saskatoon (CA); Ronald Verrall, Saskatoon (CA); Peng Yang, Shenyang (CN); Marianna Foldvari, Kitchener (CA); Jackson Chitanda, Saskatoon (CA); Deborah Michel, Saskatoon (CA)

(73) Assignee: University of Saskatchewan (CA)

( * ) Notice: Subject to any disclaimer, the term of this patent is extended or adjusted under 35 U.S.C. 154(b) by 104 days.

(21) Appl. No.: 14/118,721

(22) PCT Filed: May 18, 2012

(86) PCT No.: PCT/CA2012/000483
§ 371 (c)(1),
(2), (4) Date: Nov. 19, 2013

(87) PCT Pub. No.: WO2012/159197
PCT Pub. Date: Nov. 29, 2012

(65) Prior Publication Data
US 2014/0113977 A1    Apr. 24, 2014

Related U.S. Application Data

(60) Provisional application No. 61/488,510, filed on May 20, 2011.

(51) Int. Cl.
*A61K 47/40* (2006.01)
*A61K 47/48* (2006.01)
*C08B 37/16* (2006.01)
*B82Y 5/00* (2011.01)

(52) U.S. Cl.
CPC ........... *A61K 47/40* (2013.01); *A61K 47/48969* (2013.01); *B82Y 5/00* (2013.01); *C08B 37/0012* (2013.01); *C08B 37/0015* (2013.01)

(58) Field of Classification Search
CPC ........................ A61K 47/40; C08B 37/0012
See application file for complete search history.

(56) References Cited

U.S. PATENT DOCUMENTS

2007/0142324 A1    6/2007  Perly et al.
2009/0192205 A1    7/2009  Augustijns et al.

OTHER PUBLICATIONS

Vetvicka D, Hruby M, Hovorka O, et al. Biological evaluation of polymeric micelles with covalently bound doxorubicin. Bioconjug Chem 2009;20:2090-7.
Liang XJ, Chen C, Zhao Y, Wang PC. Circumventing tumor resistance to chemotherapy by nanotechnology. Methods Mol Biol 2010;596:467-88.
Padsis J, Turley R, Tyler D. Pharmacotherapy of regional melanoma therapy. Expert Opin Pharmacother 2010;11:79-93.
Das U, Alcorn J, Shrivastav A, et al. Design, synthesis and cytotoxic properties of novel 1-[4-(2-alkylaminoethoxy) phenylcarbonyl]-3,5-bis(arylidene)-4-piperidones and related compounds. Eur J Med Chem 2007;42:71-80.
Rosenzweig HS, Rakhmanova VA, MacDonald RC. Diquaternary ammonium compounds as transfection agents. Bioconjug Chem 2001;12:258-63.
Yu D et al. Effects of inorganic and organic salts on aggregation behavior of cationic gemini surfactants. Journal of Physical Chemistry B 2010;114:14955-64.
Du X, Chen X, Lu W, Hou J. Spectroscopic study on binding behaviors of different structural nonionic surfactants to cyclodextrins. J Colloid Interface Sci 2004;274:645-51.
Challa R, Ahuja A, Ali J, Khar RK. Cyclodextrins in drug delivery: An updated review. AAPS PharmSciTech 2005;6:E329-57.
Subramaniam D, May R, Sureban SM, Lee KB, George R, Kuppusamy P, et al. Diphenyl difluoroketone: A curcumin derivative with potent in vivo anticancer activity. Cancer Research Mar. 15, 2008;68(6):1962-1969.
Thomas SL, Zhong D, Zhou W, Malik S, Liotta D, Snyder JP, et al. EF24, a novel curcumin analog, disrupts the microtubule cytoskeleton and inhibits HIF-1. Cell Cycle Aug. 2008;7(15):2409-2417.
Tan X, Sidell N, Mancini A, Huang RP, Shenming W, Horowitz IR, et al. Multiple anticancer activities of EF24, a novel curcumin analog, on human ovarian carcinoma cells. Reprod Sci Oct. 2010;17(10):931-940.
Tantishaiyakul V, Wiwattanawongsa K, Pinsuwan S, et al. Characterization of mefenamic acid-guaiacol ester: Stability and transport across caco-2 cell monolayers. Pharm Res 2002;19:1013-8.
Yadav VR, Prasad S, Kannappan R, et al. Cyclodextrin-complexed curcumin exhibits anti-inflammatory and antiproliferative activities superior to those of curcumin through higher cellular uptake. Biochem Pharmacol 2010;80:1021-32.
Dreaden EC, Mwakwari SC, Sodji QH, Oyelere AK, El-Sayed MA. Tamoxifen-poly(ethylene glycol)-thiol gold nanoparticle conjugates: Enhanced potency and selective delivery for breast cancer treatment. Bioconjug Chem 2009;20:2247-53.
Hu CM, Zhang L. Therapeutic nanoparticles to combat cancer drug resistance. Curr Drug Metab 2009;10:836-41.
Bush JA, Cheung KJ, Jr., Li G. Curcumin induces apoptosis in human melanoma cells through a fas receptor/ caspase-8 pathway independent of p. 53. Exp Cell Res 2001;271:305-14.
Turley RS, Raymond AK, Tyler DS. Regional treatment strategies for in-transit melanoma metastasis. Surg Oncol Clin N. Am 2011;20:79-103.
Mittal S, Song X, Vig BS, Amidon GL. Proline prodrug of melphalan targeted to prolidase, a prodrug activating enzyme overexpressed in melanoma. Pharm Res 2007;24:1290-8.
Michel D, Chitanda JM, Balogh R, Yang P, Singh J, Das U, El-Aneed A, Dimmock J, Verrall R, Badea I.Design and evaluation of cyclodextrin-based delivery systems to incorporate poorly soluble curcumin analogs for the treatment of melanoma. Eur J Pharm Biopharm. Aug. 2012;81(3):548-56.

*Primary Examiner* — Wu-Cheng Winston Shen
*Assistant Examiner* — Christopher R Stone
(74) *Attorney, Agent, or Firm* — Schwegman Lundberg & Woessner, P.A.

(57) ABSTRACT

This disclosure relates to cyclodextrin-based drug delivery agents that comprise a cyclodextrin moiety covalently linked to a moiety of a gemini surfactant. Pharmaceutical compositions comprising the drug delivery agent and a therapeutic agent are also disclosed.

18 Claims, 12 Drawing Sheets

NC 2067/DMSO

NC 2067/CD

NC 2067/CDgemini

NC 2081/DMSO

NC 2081/CD

NC 2067/CDgemini

DMSO

CD

CDgemini

DRUG DELIVERY AGENTS COMPRISING CYCLODEXTRIN COVALENTLY LINKED TO A GEMINI SURFACTANT, AND PHARMACEUTICAL COMPOSITIONS COMPRISING THE SAME

RELATED APPLICATIONS

This application is a National Phase application of International Application No. PCT/2012/000483 filed on May 18, 2012, which claims the benefit of priority to U.S. provisional application No. 61/488,510 filed May 20, 2011, the contents of both of which are incorporated herein by reference in their entirety.

FIELD

This disclosure relates to drug delivery agents, and pharmaceutical compositions comprising the drug delivery agent and a therapeutic agent.

BACKGROUND

Cancer is a major cause of death worldwide and according to the Canadian Cancer Society, cancer is the leading cause of early death in Canada. One Canadian is diagnosed with cancer every four minutes, while one individual in Canada dies every eight minutes from cancer. Cancer therapy, despite formidable efforts in oncology research, remains largely ineffective. In addition to limited specificity and high overall toxicity of the anticancer agents,[1] chemoresistance is a major contributor to this inefficiency.[2] One of the cancer types that urgently needs efficient therapy is melanoma.[3] Melanoma is a malignant skin disease primarily caused by damaging UV rays from the sunlight on the genetic material in melanocytes. The number of melanoma cases has been increasing worldwide with over 200,000 cases diagnosed every year. The cost of a 5-year treatment of advanced-stage melanoma is $160,000 in the US and it is considered the most expensive neoplastic disorder.[4] The total cost for the treatment of melanoma is estimated to be $5 billion in 2010. Melanoma is considered the most dangerous of the skin diseases due to its high propensity for metastasis. Currently, there is a lack of efficient and specific non-invasive treatment for melanoma, especially for the in-transit metastatic melanoma which develops between the primary lesion and the regional lymph nodes. The prognosis for this stage is as poor as for multiple nodal metastases. The possibility of surgical resection is limited and systemic treatment is not beneficial. Isolated limb perfusion or infusion with melphalan, complicated procedures requiring highly qualified personnel and specialized equipment are the only viable therapy.[3]

SUMMARY

This application relates to pharmaceutical compositions and/or nanoparticles comprising a delivery agent and a therapeutic agent, which are optionally formulated to be suitable for a variety of routes of administration, including parenteral (intravenous, subcutaneous) and topical applications. In particular, the present disclosure relates to pharmaceutical compositions or nanoparticles comprising a delivery agent and a therapeutic agent, wherein the delivery agent comprises a cyclodextrin moiety, or derivative thereof, conjugated to a gemini surfactant moiety through a linker moiety, wherein the delivery agent complexes with the therapeutic agent and aids in the delivery of the therapeutic agent, optionally through the skin when formulated for topical administration.

Accordingly, the present disclosure includes a pharmaceutical composition comprising a drug delivery agent and a therapeutic agent, wherein the drug delivery agent comprises a compound of the formula (I):

$$CD-L-G \qquad (I)$$

wherein,
CD is a cyclodextrin moiety or a derivative thereof;
L is a linker moiety; and
G is a moiety of a gemini surfactant.

In another embodiment, the linker moiety L is $(C_1-C_{20})$-alkylene, $(C_2-C_{20})$-alkenylene, $(C_2-C_{20})$-alkynylene, $(C_3-C_{10})$-cycloalkylene, or any combination thereof, wherein said 4 groups are optionally substituted by one or more groups selected from halo, (=O), $OR^1$ or $R^1$, in which $R^1$ is selected from $(C_1-C_6)$-alkyl, $(C_2-C_6)$-alkenyl, $(C_2-C_6)$-alkynyl or $(C_3-C_6)$-cycloalkyl, and wherein one or more carbon atoms in said 4 groups is optionally replaced with a heteromoiety selected from O, S, N, NH or $N(C_1-C_6)$-alkyl.

In one embodiment, the gemini surfactant G is a moiety of the formula (II):

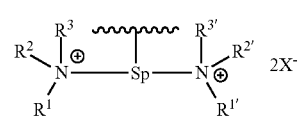

$$(II)$$

wherein $R^1$ and $R^{1'}$ are independently or simultaneously $(C_5-C_{30})$-alkyl, $(C_5-C_{30})$-alkenyl, $(C_5-C_{30})$-alkynyl or $(C_6-C_{16})$-aryl, all 3 groups optionally substituted by one or more groups selected from halo, $OR^4$ or $R^4$, in which $R^4$ is selected from $(C_1-C_6)$-alkyl, $(C_2-C_6)$-alkenyl, $(C_2-C_6)$-alkynyl or $(C_3-C_6)$-cycloalkyl, and wherein one or more carbon atoms in said 3 groups is optionally replaced with a heteromoiety selected from O, S, N, NH or $N(C_1-C_6)$-alkyl;
$R^2$, $R^3$, $R^{2'}$ and $R^{3'}$ are independently or simultaneously $(C_1-C_{10})$-alkyl, $(C_2-C_{10})$-alkenyl or $(C_2-C_{10})$-alkynyl all 3 groups optionally substituted by one or more groups selected from halo, $OR^5$ or $R^5$, in which $R^5$ is selected from $(C_1-C_6)$-alkyl, $(C_2-C_6)$-alkenyl, $(C_2-C_6)$-alkynyl or $(C_3-C_6)$-cycloalkyl;
Sp is a spacer moiety bonded to the linker moiety L; and
X is any suitable anionic counterion.

In another embodiment, the spacer moiety Sp is $(C_1-C_{20})$-alkylene, $(C_2-C_{20})$-alkenylene, $(C_2-C_{20})$-alkynylene, $(C_3-C_{10})$-cycloalkylene, or any combination thereof, wherein said 4 groups are optionally substituted by one or more groups selected from halo, $OR^5$ or $R^5$, in which $R^5$ is selected from $(C_1-C_6)$-alkyl, $(C_2-C_6)$-alkenyl, $(C_2-C_6)$-alkynyl or $(C_3-C_6)$-cycloalkyl, and wherein one or more carbon atoms in said 4 groups is optionally replaced with a heteromoiety selected from O, S, N, NH or $N(C_1-C_6)$-alkyl.

In another embodiment, the cyclodextrin moiety is a β-cyclodextrin moiety, or a derivative thereof.

In one embodiment, the compound of formula (I) is

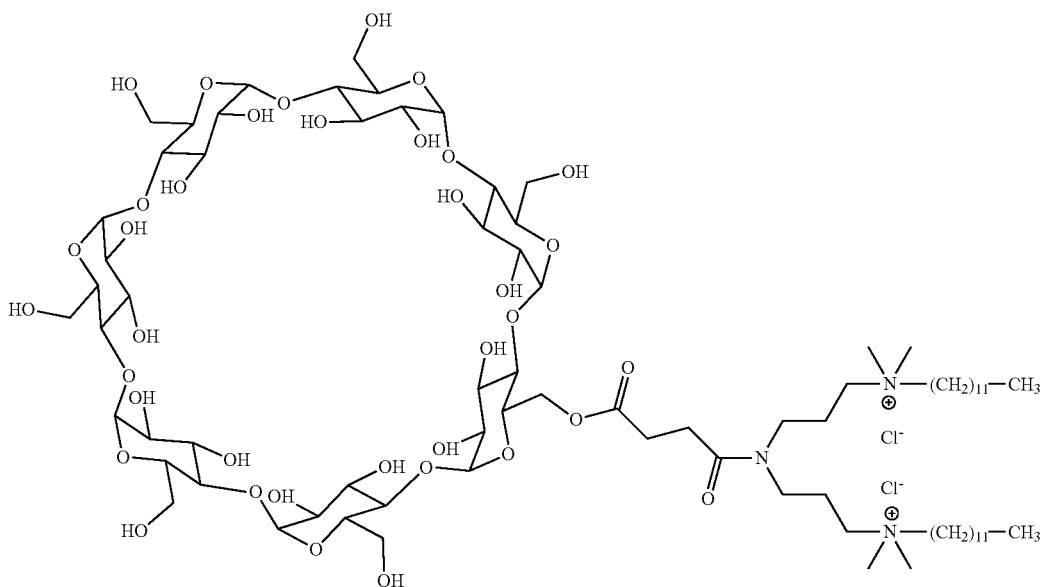

In one embodiment, the therapeutic agent is lipophilic. In another embodiment, the therapeutic agent comprises an antineoplastic agent. In another embodiment, the antineoplastic agent is a lipophilic antineoplastic agent.

The present disclosure also includes a nanoparticulate delivery agent comprising a compound of the formula (I) as defined above for the delivery of therapeutic agents.

The present disclosure also includes a method of treating melanoma in a mammal comprising topically administering to the mammal a therapeutically effective amount of a composition according to the disclosure. In another embodiment, the present disclosure also includes a method for inhibiting the growth of a melanoma cell, comprising contacting the melanoma cell with a therapeutically effective amount of a composition of the disclosure.

Further aspects and advantages of the embodiments described herein will appear from the following description taken together with the accompanying drawing.

BRIEF DESCRIPTION OF THE DRAWINGS

For a better understanding of the embodiments described herein and to show more clearly how they may be carried into effect, reference will now be made, by way of example only, to the accompanying drawing which shows at least one exemplary embodiment, and in which.

DETAILED DESCRIPTION (I) Definitions

Figure 1:
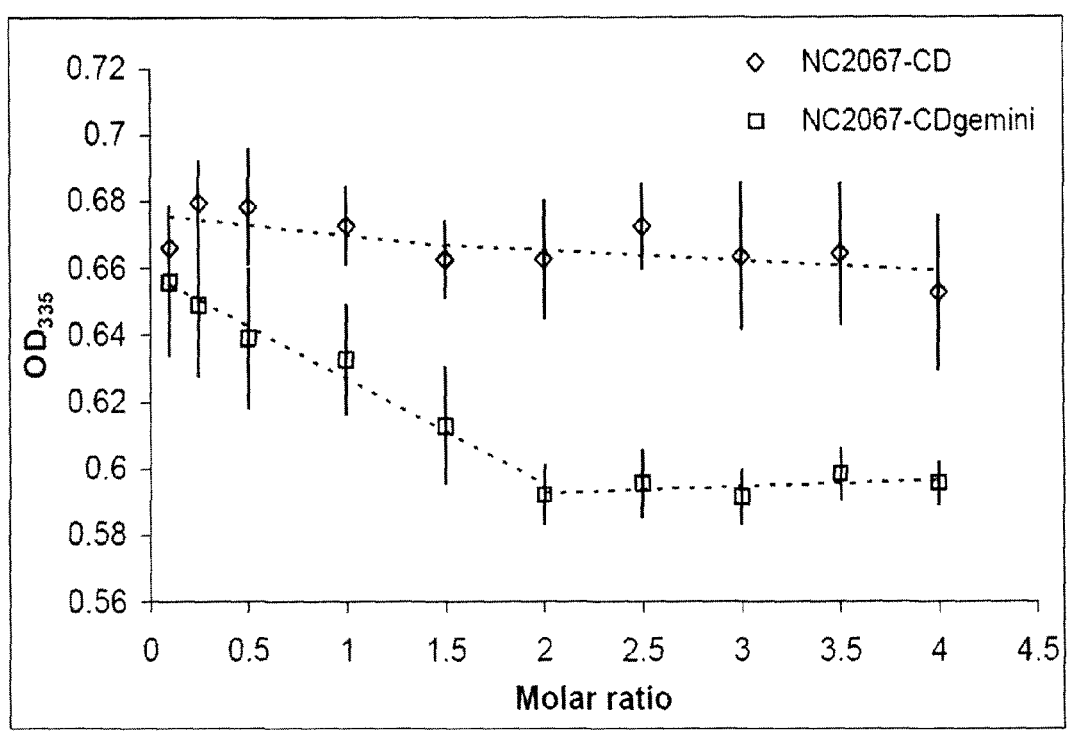
FIG. 1 is a graph showing optical densities in an embodiment of the disclosure of a therapeutic agent with CD or CDgemini as a function of increasing mole ratio of delivery agent to therapeutic agent.

The term "drug delivery agent" as used herein refers to compounds of the formula (I) which aid in the administration of a therapeutic agent to a mammal, suitably for a variety of administration routes, including topical application. For example, the drug delivery agent aids in the transport of the therapeutic agent into the tissue (e.g. skin, mucosal surfaces) through permeation barriers (such as the stratum corneum and mucosal membranes) and cellular uptake of the nanoparticulate system.

The term "nanoparticle", as used herein, is meant to refer to particles, the average dimensions or diameters of which are less than 500 nm.

The term "therapeutic agent" as used herein refers to any therapeutic agent, drug, active agent, medicament, and/or medicine which is suitable for topical (e.g. dermal, oral, rectal, vaginal or ocular), oral and parenteral administration using the drug delivery agent of the disclosure that includes its pharmaceutically acceptable forms, as well as in the anhydrous, hydrated, and solvated forms, in the form of prodrugs, and in the individually optically active enantiomers of the agent. For example, the therapeutic agent is an anti-neoplastic agent, which is optionally a lipophilic anti-neoplastic agent, psychotropic lipophilic drugs or other drug families with lipophilic nature. Other therapeutic agents include psychotropic agents (for example, cyclic antidepressants) and antiretroviral anti-viral medications, such as HIV medications (for example ritonavir or saquinavir).

The term "lipophilic" as used herein, with respect to therapeutic agents, is a term well known in the art, and generally refers to lipophilic molecules having a partition coefficient (log p) in octanol/water of greater than 1.0, optionally greater than 3.0. Lipophilic therapeutic agents are drugs which are poorly soluble, or substantially insoluble, in water at 25° C.

The term "cyclodextrin" as used herein refers to a cyclic oligosaccharide moiety composed of 5 or more α-D-glucopyranoside units linked through α-(1,4) glucosidic bonds, and includes derivatives thereof.

The term "derivative" as used herein refers to a substance which comprises the same basic carbon skeleton and functionality as the parent compound, but can also bear one or more substituents or substitutions of the parent compound. For example, ester derivatives of cyclodextrin would include any compounds in which, in one embodiment, free hydroxyl groups of the cyclodextrin have been esterified (e.g. methyl esters, ethyl esters, benzyl esters etc.).

The term "linker" as used herein refers to any divalent moiety or group capable of bonding to the cyclodextrin moiety and the gemini surfactant moiety, and is therefore usually bifunctional. As such, the linker, prior to incorporation into the compound of formula (I) has an appropriate functional group at each end.

The term "gemini surfactant" as used herein refers to a moiety comprising a spacer moiety separating two cationic surfactant moieties, wherein the cationic surfactant moieties comprise a hydrophobic tail group and a cationic head group, in which the two surfactant moieties are the same or different. For example, the cationic head group optionally comprises a quaternary nitrogen group (ammonium moiety) bonded to a hydrophobic tail and the spacer, as well as two other moieties.

The term "spacer" as used herein refers to any trivalent moiety or group capable of bonding to the surfactant moieties of the gemini surfactant, and also bond to the linker moiety.

The phrase "therapeutically effective amount" as used herein refers to the amount of the pharmaceutical composition, which provides a therapeutic benefit in the prevention, treatment, or management, of the disease being treated. For example, when a pharmaceutical composition of the disclosure is formulated for the topical administration of melanoma, the therapeutically effective amount refers to an amount of the therapeutic agent which is able to treat or control the melanoma. Different therapeutically effective amounts may be applicable for each disorder, as will be readily known or determined by those of ordinary skill in the art.

The term "$C_{n-w}$alkyl" as used herein means straight and/or branched chain, saturated alkyl groups containing from "n" to "w" carbon atoms and includes (depending on the identity of n and w) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the lowest number of carbon atoms and w is an integer representing the largest number of carbon atoms in the alkyl group.

The term "$C_{2-w}$alkenyl" as used herein means straight and/ or branched chain, unsaturated alkyl groups containing from two to w carbon atoms and one to three double bonds, and includes (depending on the identity of w) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable w is an integer representing the largest number of carbon atoms in the alkenyl group.

The term "$C_{2-w}$alkynyl" as used herein means straight and/ or branched chain, unsaturated alkyl groups containing from two to w carbon atoms and one to three bonds, and includes (depending on the identity of w) propargyl, 2-methylprop-1-ynyl, but-1-ynyl, but-2-ynyl, but-3-ynyl, 2-methylbut-1-ynyl, 2-methylpent-1-ynyl, 4-methylpent-1-ynyl, 4-methylpent-2-ynyl, 2-methylpent-2-ynyl, 4-methylpenta-1,3-diynyl, hexyn-1-yl and the like, where the variable w is an integer representing the largest number of carbon atoms in the alkynyl group.

The term "$C_{3-w}$cycloalkyl" as used herein means a monocyclic, bicyclic or tricyclic saturated carbocylic group containing from three to w carbon atoms and includes (depending on the identity of w) cyclopropyl, cyclobutyl, cyclopentyl, cyclodecyl and the like, where the variable w is an integer representing the largest number of carbon atoms in the cycloalkyl group.

The term "$(C_6-C_z)$-aryl" as used herein means a monocyclic, bicyclic, tricyclic or tetracyclic aromatic ring system containing from 6 to z carbon atoms and includes (depending on the identity of z) phenyl, naphthyl, anthracenyl, 1,2-dihydronaphthyl, 1,2,3,4-tetrahydronaphthyl, fluorenyl, pyene, indanyl, indenyl and the like.

The suffix "ene" added on to any of the above groups means that the group is divalent, i.e. inserted between two other groups. When the group is a ring system, the two other groups may be located at any location on the ring system, including at adjacent and non-adjacent nodes.

The term "anionic counterion" as used herein refers to any negatively charged ion that is commonly used as a counterion, such as halo (such as chloro), $C_{1-6}$alkoxy and carboxyl (C(=O)O).

(II) Delivery Agents

The present disclosure relates to drug delivery agents for the delivery of therapeutic agents. In particular, the delivery agent comprises a compound of the formula (I):

CD-L-G        (I)

wherein,
CD is a cyclodextrin moiety, or a derivative thereof;
L is a linker moiety; and
G is a moiety of a gemini surfactant.

In one embodiment of the disclosure, the linker moiety L is $(C_1-C_{20})$-alkylene, $(C_2-C_{20})$-alkenylene, $(C_2-C_{20})$-alkynylene, $(C_3-C_{10})$-cycloalkylene, or any combination thereof, wherein said 4 groups are optionally substituted by one or more groups selected from halo, (=O), OR$^1$ or R$^1$, in which R$^1$ is selected from $(C_1-C_6)$-alkyl, $(C_2-C_6)$-alkenyl, $(C_2-C_6)$-alkynyl or $(C_3-C_6)$-cycloalkyl, and wherein one or more carbon atoms in said 4 groups is optionally replaced with a heteromoiety selected from O, S, N, NH or N($C_1-C_6$)-alkyl. In another embodiment, the linker moiety L is $(C_1-C_{10})$-alkylene, $(C_2-C_{10})$-alkenylene, $(C_2-C_{10})$-alkynylene, $(C_3-C_8)$-cycloalkylene, or any combination thereof. In a further embodiment, the linker moiety L is $(C_1-C_4)$-alkylene, $(C_2-C_4)$-alkenylene, $(C_2-C_4)$-alkynylene, $(C_5-C_6)$-cycloalkylene, or any combination thereof. In another embodiment, the linker moiety L is $(C_2-C_{10})$-alkylene substituted twice by (=O).

In one embodiment of the disclosure, the linker moiety L is

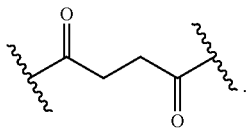 [SMILES: *C(=O)CCC(*)=O]

In one embodiment of the disclosure, the gemini surfactant G is a moiety of the formula (II):

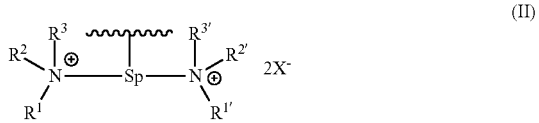

wherein $R^1$ and $R^{1'}$ are independently or simultaneously $(C_5\text{-}C_{30})$-alkyl, $(C_5\text{-}C_{30})$-alkenyl, $(C_5\text{-}C_{30})$-alkynyl or $(C_6\text{-}C_{16})$-aryl, all 3 groups optionally substituted by one or more groups selected from halo, $OR^4$ or $R^4$, in which $R^4$ is selected from $(C_1\text{-}C_6)$-alkyl, $(C_2\text{-}C_6)$-alkenyl, $(C_2\text{-}C_6)$-alkynyl or $(C_3\text{-}C_6)$-cycloalkyl, and wherein one or more carbon atoms in said 3 groups is optionally replaced with a heteromoiety selected from O, S, N, NH or $N(C_1\text{-}C_6)$-alkyl;

$R^2$, $R^3$, $R^{2'}$ and $R^{3'}$ are independently or simultaneously $(C_1\text{-}C_{10})$-alkyl, $(C_2\text{-}C_{10})$-alkenyl or $(C_2\text{-}C_{10})$-alkynyl all 3 groups optionally substituted by one or more groups selected from halo, $OR^5$ or $R^5$, in which $R^5$ is selected from $(C_1\text{-}C_6)$-alkyl, $(C_2\text{-}C_6)$-alkenyl, $(C_2\text{-}C_6)$-alkynyl or $(C_3\text{-}C_6)$-cycloalkyl;

Sp is a spacer moiety bonded to the linker moiety L; and

X is any suitable anionic counterion.

In one embodiment of the disclosure, $R^1$ and $R^{1'}$ are independently or simultaneously $(C_{10}\text{-}C_{22})$-alkyl, $(C_{10}\text{-}C_{22})$-alkenyl, $(C_{10}\text{-}C_{22})$-alkynyl or $(C_6\text{-}C_{10})$-aryl. In another embodiment, $R^1$ and $R^{1'}$ are independently or simultaneously $(C_{10}\text{-}C_{12})$-alkyl, $(C_{10}\text{-}C_{12})$-alkenyl or $(C_{10}\text{-}C_{12})$-alkynyl. In another embodiment, $R^1$ and $R^{1'}$ are $C_{12}$-alkyl.

In another embodiment, $R^2$, $R^3$, $R^{2'}$ and $R^{3'}$ are independently or simultaneously $(C_1\text{-}C_6)$-alkyl, $(C_2\text{-}C_6)$-alkenyl or $(C_2\text{-}C_6)$-alkynylene. In a further embodiment, $R^2$, $R^3$, $R^{2'}$ and $R^{3'}$ are independently or simultaneously $(C_1\text{-}C_3)$-alkyl, $(C_2\text{-}C_3)$-alkenyl or $(C_2\text{-}C_3)$-alkynylene. In a further embodiment, $R^2$, $R^3$, $R^{2'}$ and $R^{3'}$ are independently or simultaneously methyl, ethyl, propyl or iso-propyl. In a further embodiment, $R^2$, $R^3$, $R^{2'}$ and $R^{3'}$ are methyl.

In another embodiment of the disclosure, the spacer moiety Sp is $(C_1\text{-}C_{10})$-alkylene, $(C_2\text{-}C_{20})$-alkenylene, $(C_2\text{-}C_{20})$-alkynylene, $(C_3\text{-}C_{10})$-cycloalkylene, or any combination thereof, wherein said 4 groups are optionally substituted by one or more groups selected from halo, $OR^5$ or $R^5$, in which $R^5$ is selected from $(C_1\text{-}C_6)$-alkyl, $(C_2\text{-}C_6)$-alkenyl, $(C_2\text{-}C_6)$-alkynyl or $(C_3\text{-}C_6)$-cycloalkyl, and wherein one or more carbon atoms in said 4 groups is optionally replaced with a heteromoiety selected from O, S, N, NH or $N(C_1\text{-}C_6)$-alkyl. In a further embodiment, the spacer moiety Sp is $(C_1\text{-}C_{10})$-alkylene, $(C_2\text{-}C_{10})$-alkenylene, $(C_2\text{-}C_{10})$-alkynylene, $(C_3\text{-}C_6)$-cycloalkylene, or any combination thereof. In another embodiment, the spacer moiety Sp is $(C_1\text{-}C_8)$-alkylene, wherein one or more carbon atoms in said group is optionally replaced with a heteromoiety selected from O, S, N, NH or $N(C_1\text{-}C_6)$-alkyl. In another embodiment, the spacer moiety is a $C_7$-alkylene moiety, wherein one or more carbon atoms is optionally replaced with a nitrogen atom.

In another embodiment, the spacer moiety Sp is

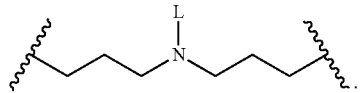

In one embodiment, the gemini surfactant moieties conjugated to the cyclodextrin moieties of the compounds of formula (I) self-assemble into cationic nanoparticles and act as efficient in vivo cutaneous permeation enhancers for therapeutic agents. Without being bound by theory, the gemini surfactant moieties demonstrate lower cellular toxicity[5], higher efficiency in reducing surface tension, and greater tendency to self-assemble compared to monovalent permeation enhancers[6].

In another embodiment of the disclosure, $X^-$ is a halogen ion.

In an embodiment of the disclosure, the gemini surfactant moiety is

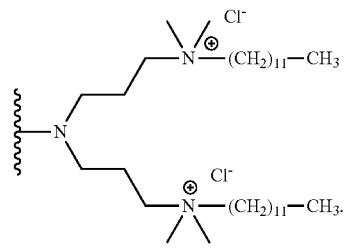

In an embodiment of the disclosure, the cyclodextrin moiety, or derivative thereof, is a moiety of α-cyclodextrin, β-cyclodextrin or γ-cyclodextrin. In another embodiment, the cyclodextrin moiety is a β-cyclodextrin moiety, or a derivative thereof.

In one embodiment, the cyclodextrin moiety comprises an amphiphilic moiety which incorporates lipophilic therapeutic agents into the cyclodextrin pocket[7], while the gemini surfactant moiety is able to interact, electrostatically, with negatively charged cell surfaces through the cationic head groups (such as quaternary ammonium groups). In one embodiment, the compounds of formula (I) self-assemble into micelle/nanoparticle-like structures by means of hydrophobic interactions between the hydrocarbon chains attached to the polar nitrogen head groups, which trigger cellular uptake of the nanostructures by endocytosis.

In one embodiment, the cyclodextrin moiety creates a relatively lipophilic inner cavity and hydrophilic outer surface. Accordingly, in one embodiment, therapeutic agents, for example lipophilic therapeutic agents, form non-covalent inclusion complexes with the interior cavity of the cyclodextrin moiety in an aqueous environment.[8] Without being bound by theory, these properties of the compounds of formula (I) result in enhanced drug absorption.

In another embodiment, the drug delivery agent of the formula (I) is a nanoparticle.

In an embodiment of the disclosure, the compound of formula (I) is

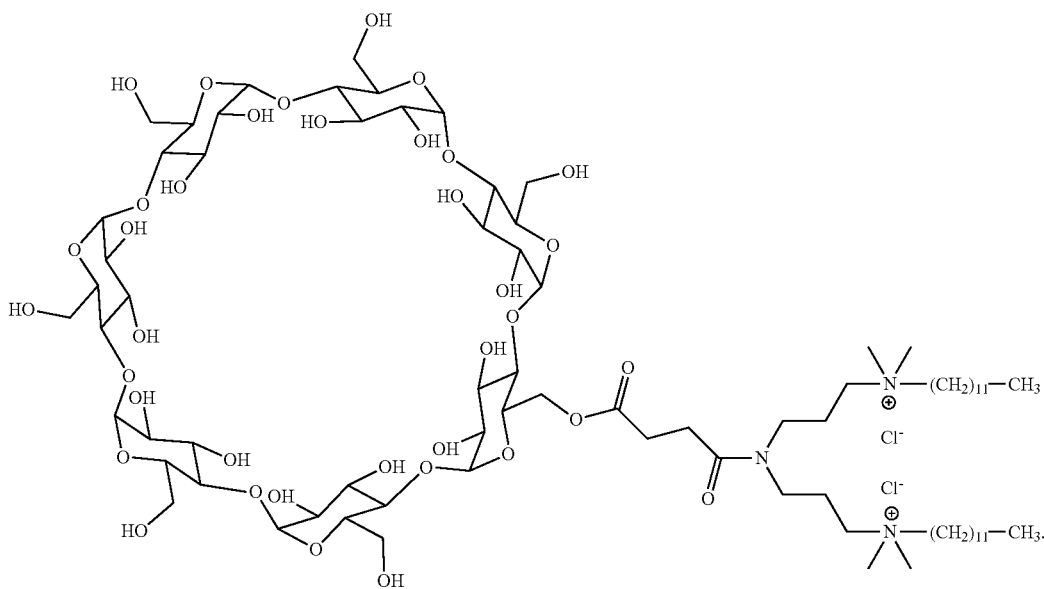

After preparation of the drug delivery agent of the formula (I), the compounds of the formula (I) are mixed with a therapeutic agent for a time sufficient for the drug delivery agent to complex with the therapeutic agent (and optionally other pharmaceutical excipients), resulting in a pharmaceutical composition which is suitable to treat conditions intended to be treated with the therapeutic agent.

(II) Pharmaceutical Compositions

The present disclosure also relates to pharmaceutical compositions, optionally suitable for topical administration, and optionally suitable for the treatment of a cancer such as melanoma. In particular, the pharmaceutical compositions comprise a drug delivery agent which aids in the delivery of a therapeutic agent.

Accordingly, the present disclosure includes a pharmaceutical composition comprising a drug delivery agent and a therapeutic agent, wherein the drug delivery agent comprises a compound of the formula (I):

CD-L-G      (I)

wherein,
CD is a cyclodextrin moiety, or a derivative thereof;
L is a linker moiety; and
G is a moiety of a gemini surfactant.

In one embodiment of the disclosure, the linker moiety L is $(C_1-C_{20})$-alkylene, $(C_2-C_{20})$-alkenylene, $(C_2-C_{20})$-alkynylene, $(C_3-C_{10})$-cycloalkylene, or any combination thereof, wherein said 4 groups are optionally substituted by one or more groups selected from halo, (=O), $OR^1$ or $R^1$, in which $R^1$ is selected from $(C_1-C_6)$-alkyl, $(C_2-C_6)$-alkenyl, $(C_2-C_6)$-alkynyl or $(C_3-C_6)$-cycloalkyl, and wherein one or more carbon atoms in said 4 groups is optionally replaced with a heteromoiety selected from O, S, N, NH or $N(C_1-C_6)$-alkyl. In another embodiment, the linker moiety L is $(C_1-C_{10})$-alkylene, $(C_2-C_{10})$-alkenylene, $(C_2-C_{10})$-alkynylene, $(C_3-C_8)$-cycloalkylene, or any combination thereof. In a further embodiment, the linker moiety L is $(C_1-C_4)$-alkylene, $(C_2-C_4)$-alkenylene, $(C_2-C_4)$-alkynylene, $(C_5-C_6)$-cycloalkylene, or any combination thereof. In another embodiment, the linker moiety L is $(C_2-C_{10})$-alkylene substituted twice by (=O).

In one embodiment of the disclosure, the linker moiety L is

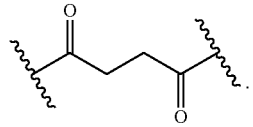 [SMILES: *C(=O)CCC(*)=O]

In one embodiment of the disclosure, the gemini surfactant G is a moiety of the formula (II):

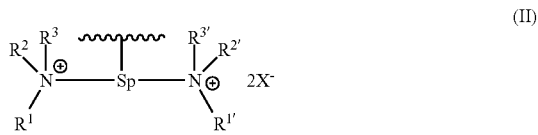

(II)

wherein $R^1$ and $R^{1'}$ are independently or simultaneously $(C_5-C_{30})$-alkyl, $(C_5-C_{30})$-alkenyl, $(C_5-C_{30})$-alkynyl or $(C_6-C_{16})$-aryl, all 3 groups optionally substituted by one or more groups selected from halo, $OR^4$ or $R^4$, in which $R^4$ is selected from $(C_1-C_6)$-alkyl, $(C_2-C_6)$-alkenyl, $(C_2-C_6)$-alkynyl or $(C_3-C_6)$-cycloalkyl, and wherein one or more carbon atoms in said 3 groups is optionally replaced with a heteromoiety selected from O, S, N, NH or $N(C_1-C_6)$-alkyl;
$R^2$, $R^3$, $R^{2'}$ and $R^{3'}$ are independently or simultaneously $(C_1-C_{10})$-alkyl, $(C_2-C_{10})$-alkenyl or $(C_2-C_{10})$-alkynyl all 3 groups optionally substituted by one or more groups selected from halo, $OR^5$ or $R^5$, in which $R^5$ is selected from $(C_1-C_6)$-alkyl, $(C_2-C_6)$-alkenyl, $(C_2-C_6)$-alkynyl or $(C_3-C_6)$-cycloalkyl;
Sp is a spacer moiety bonded to the linker moiety L; and
X is any suitable anionic counterion.

In one embodiment of the disclosure, $R^1$ and $R^{1'}$ are independently or simultaneously $(C_{10}-C_{22})$-alkyl, $(C_{10}-C_{22})$-alkenyl, $(C_{10}-C_{22})$-alkynyl or $(C_6-C_{10})$-aryl. In another embodiment, $R^1$ and $R^{1'}$ are independently or simultaneously $(C_{10}$-

$C_{12}$)-alkyl, ($C_{10}$-$C_{12}$)-alkenyl or ($C_{10}$-$C_{12}$)-alkynyl. In another embodiment, $R^1$ and $R^{1'}$ are $C_{12}$-alkyl.

In another embodiment, $R^2$, $R^3$, $R^{2'}$ and $R^{3'}$ are independently or simultaneously ($C_1$-$C_6$)-alkyl, ($C_2$-$C_6$)-alkenyl or ($C_2$-$C_6$)-alkynylene. In a further embodiment, $R^2$, $R^3$, $R^{2'}$ and $R^{3'}$ are independently or simultaneously ($C_1$-$C_3$)-alkyl, ($C_2$-$C_3$)-alkenyl or ($C_2$-$C_3$)-alkynylene. In a further embodiment, $R^2$, $R^3$, $R^{2'}$ and $R^{3'}$ are independently or simultaneously methyl, ethyl, propyl or iso-propyl. In a further embodiment, $R^2$, $R^3$, $R^{2'}$ and $R^{3'}$ are methyl.

In another embodiment of the disclosure, the spacer moiety Sp is ($C_1$-$C_{10}$)-alkylene, ($C_2$-$C_{20}$)-alkenylene, ($C_2$-$C_{20}$)-alkynylene, ($C_3$-$C_{10}$)-cycloalkylene, or any combination thereof, wherein said 4 groups are optionally substituted by one or more groups selected from halo, $OR^5$ or $R^5$, in which $R^5$ is selected from ($C_1$-$C_6$)-alkyl, ($C_2$-$C_6$)-alkenyl, ($C_2$-$C_6$)-alkynyl or ($C_3$-$C_6$)-cycloalkyl, and wherein one or more carbon atoms in said 4 groups is optionally replaced with a heteromoiety selected from O, S, N, NH or N($C_1$-$C_6$)-alkyl. In a further embodiment, the spacer moiety Sp is ($C_1$-$C_{10}$)-alkylene, ($C_2$-$C_{10}$)-alkenylene, ($C_2$-$C_{10}$)-alkynylene, ($C_3$-$C_6$)-cycloalkylene, or any combination thereof. In another embodiment, the spacer moiety Sp is ($C_1$-$C_8$)-alkylene, wherein one or more carbon atoms in said group is optionally replaced with a heteromoiety selected from O, S, N, NH or N($C_1$-$C_6$)-alkyl. In another embodiment, the spacer moiety is a $C_7$-alkylene moiety, wherein one or more carbon atoms is optionally replaced with a nitrogen atom.

In another embodiment, the spacer moiety Sp is

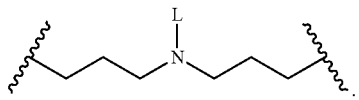

In one embodiment, the gemini surfactant moieties conjugated to the cyclodextrin moieties of the compounds of formula (I) self-assemble into cationic nanoparticles and act as efficient in vivo cutaneous permeation enhancers for therapeutic agents. Without being bound by theory, the gemini surfactant moieties demonstrate lower cellular toxicity[5], higher efficiency in reducing surface tension, and greater tendency to self-assemble compared to monovalent permeation enhancers[6].

In another embodiment of the disclosure, $X^-$ is a halogen ion.

In an embodiment of the disclosure, the gemini surfactant moiety is

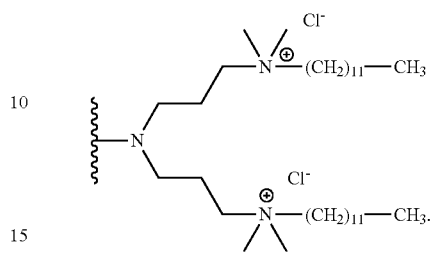

In an embodiment of the disclosure, the cyclodextrin moiety, or derivative thereof, is a moiety of α-cyclodextrin, β-cyclodextrin or γ-cyclodextrin. In another embodiment, the cyclodextrin moiety is a β-cyclodextrin moiety, or a derivative thereof.

In one embodiment, the cyclodextrin moiety comprises an amphiphilic moiety which incorporates lipophilic therapeutic agents into the cyclodextrin pocket[7], while the gemini surfactant moiety is able to interact, electrostatically, with negatively charged cell surfaces through the cationic head groups (such as quaternary ammonium groups). In one embodiment, the compounds of formula (I) self-assemble into micelle/nanoparticle-like structures by means of hydrophobic interactions between the hydrocarbon chains attached to the polar nitrogen head groups, which trigger cellular uptake of the nanostructures by endocytosis.

In one embodiment, the cyclodextrin moiety creates a relatively lipophilic inner cavity and hydrophilic outer surface. Accordingly, in one embodiment, lipophilic therapeutic agents form non-covalent inclusion complexes with the interior cavity of the cyclodextrin moiety in an aqueous environment.[8] Without being bound by theory, these properties of the compounds of formula (I) result in enhanced drug absorption.

In another embodiment, the drug delivery agent of the formula (I) is a nanoparticle.

In an embodiment of the disclosure, the compound of formula (I) is

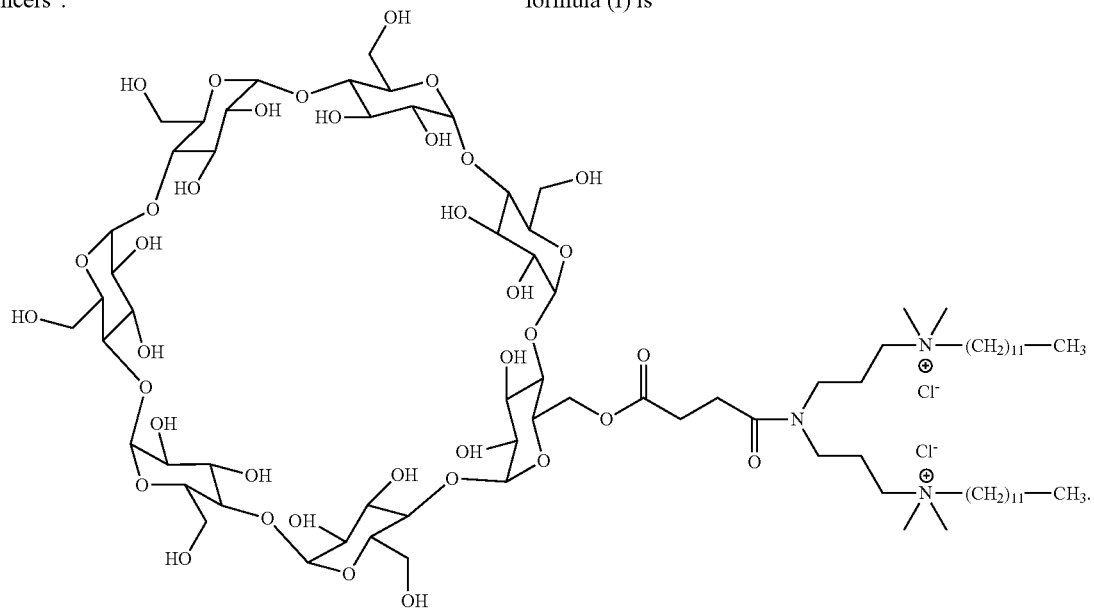

In one embodiment, the therapeutic agent is lipophilic. In another embodiment of the disclosure, the therapeutic agent comprises an antineoplastic agent. In another embodiment, the antineoplastic agent is a antineoplastic agent. In another embodiment, the antineoplastic agent is a lipophilic antineoplastic agent. Examples of therapeutic agents include curcumin (A), or a curcumin analog (B).

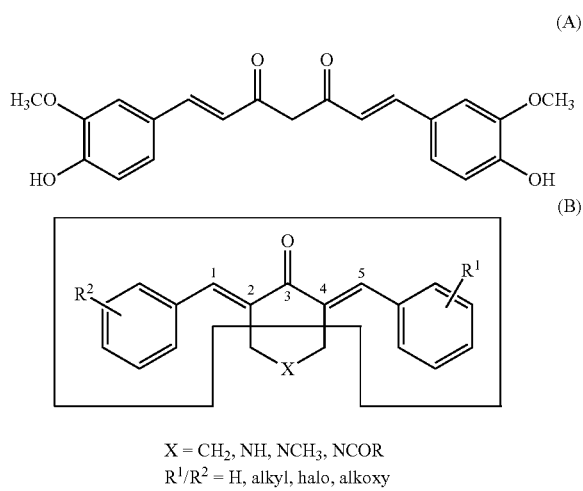

X = CH$_2$, NH, NCH$_3$, NCOR
R$^1$/R$^2$ = H, alkyl, halo, alkoxy

Examples of lipophilic antineoplastic agents include (curcumin analogs) A-NC-2067 or B-NC-2081:

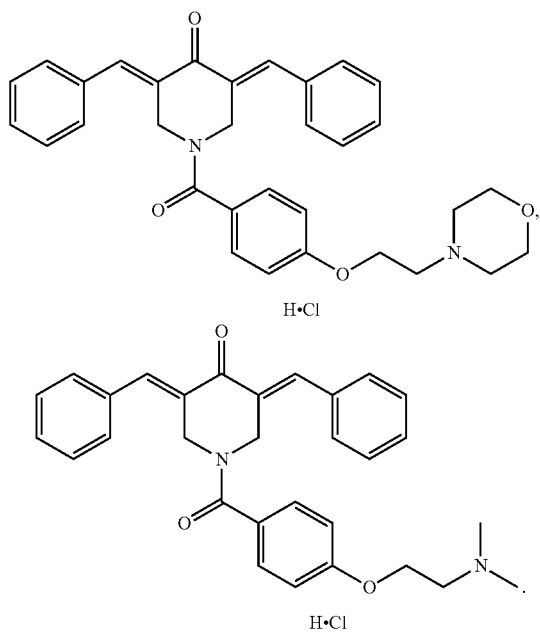

In another embodiment, the curcumin derivative is EF24, a diphenyl difluoroketone.[9-11]

In another embodiment, the therapeutic agents comprise compounds which are lipophilic and have log P values greater than about 3.0, for example 5.9 and 5.4. In one embodiment, therapeutic agents that are lipophilic in nature (log P values in the range between 3-10, optionally 5-10, or suitably 3.5-4) penetrate through the stratum corneum more readily than ionic or polar molecules,[12] which is governed by passive diffusion, since the stratum corneum consists of flattened keratinized anucleated dead cells without an active transport system. However, the lipophilic nature of certain therapeutic agents may be an impediment in cellular uptake once a drug reaches the viable tissue due to the complexity of the passage through the cellular membrane. In the viable layer, cellular uptake encompasses passive diffusion, active transport by transporter molecules and/or endocytosis.[13] Conversely to the properties of the stratum corneum, penetration of a drug into living cells is hindered by lipophilicity (log P values above 3.0).[12] Consequently, without being bound by theory, and in one embodiment, for lipohilic therapeutic agents, cellular uptake represents the rate limiting step for reaching the intracellular target for biological activity.

In one embodiment, compounds of the formula (I) are in the form of nanoparticles having a diameter of between 100 nm to 500 nm, optionally 125 nm to 250 nm, or 140 nm to 160 nm, or about 150 nm. Without being bound by theory, the nanoparticulate nature of the delivery agent facilitate active cellular uptake,[14] and therefore aids in the delivery of the therapeutic agent to where it is needed. In addition, in one embodiment, nanoparticles consisting of compounds of the formula (I), wherein the therapeutic agent is an anticancer agent, have the ability to overcome drug resistance often associated with conventional naked drug molecules.[15]

In one embodiment, the pharmaceutical compositions of the present disclosure comprising compounds of the formula (I) and a therapeutic agent demonstrate a slow continuous release of the therapeutic agent, and also a circumvention of the drug efflux by endocytotic uptake.

In another embodiment, the composition is suitable for topical administration. In another embodiment, the compositions of the disclosure are suitable for oral administration and the compositions improve the bioavailability of the therapeutic agent after oral administration.

In another embodiment, the compositions are suitable for mucosal (such as nasal, rectal, vaginal and buccal) administration for treatment of conditions of the oral mucosa and the eye (oral and uveal mucosa). In another embodiment, the compositions are suitable for parenteral (intravenous and subcutaneous) administration.

The production of pharmaceutical preparations can be effected in a manner which will be familiar to any person skilled in the art by bringing the described compounds of formula (I) and a therapeutic agent, (i) together with suitable, non-toxic, inert, therapeutically compatible solid or liquid carrier materials and, if desired, usual pharmaceutical adjuvants.

Suitable carrier materials are not only inorganic carrier materials, but also organic carrier materials. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, salts for varying the osmotic pressure, buffer substances, solubilizers, colorants and antioxidants come into consideration as pharmaceutical adjuvants.

(III) Nanoparticles

The present disclosure also includes nanoparticles comprising a drug delivery agent of the formula (I). Accordingly, the nanoparticles comprise a compound of the formula (I):

CD-L-G (I)

wherein,
CD is a cyclodextrin moiety, or a derivative thereof;
L is a linker moiety; and
G is a moiety of a gemini surfactant.

In one embodiment of the disclosure, the linker moiety L is $(C_1-C_{20})$-alkylene, $(C_2-C_{20})$-alkenylene, $(C_2-C_{20})$-alkynylene, $(C_3-C_{10})$-cycloalkylene, or any combination thereof, wherein said 4 groups are optionally substituted by one or more groups selected from halo, (=O), $OR^1$ or $R^1$, in which $R^1$ is selected from $(C_1-C_6)$-alkyl, $(C_2-C_6)$-alkenyl, $(C_2-C_6)$-alkynyl or $(C_3-C_6)$-cycloalkyl, and wherein one or more carbon atoms in said 4 groups is optionally replaced with a heteromoiety selected from O, S, N, NH or $N(C_1-C_6)$-alkyl. In another embodiment, the linker moiety L is $(C_1-C_{10})$-alkylene, $(C_2-C_{10})$-alkenylene, $(C_2-C_{10})$-alkynylene, $(C_3-C_8)$-cycloalkylene, or any combination thereof. In a further embodiment, the linker moiety L is $(C_1-C_4)$-alkylene, $(C_2-C_4)$-alkenylene, $(C_2-C_4)$-alkynylene, $(C_5-C_6)$-cycloalkylene, or any combination thereof. In another embodiment, the linker moiety L is $(C_2-C_{10})$-alkylene substituted twice by (=O).

In one embodiment of the disclosure, the linker moiety L is

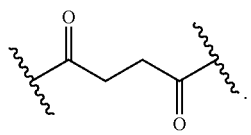

In one embodiment of the disclosure, the gemini surfactant G is a moiety of the formula (II):

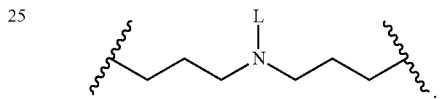

(II)

wherein $R^1$ and $R^{1'}$ are independently or simultaneously $(C_5-C_{30})$-alkyl, $(C_5-C_{30})$-alkenyl, $(C_5-C_{30})$-alkynyl or $(C_6-C_{16})$-aryl, all 3 groups optionally substituted by one or more groups selected from halo, $OR^4$ or $R^4$, in which $R^4$ is selected from $(C_1-C_6)$-alkyl, $(C_2-C_6)$-alkenyl, $(C_2-C_6)$-alkynyl or $(C_3-C_6)$-cycloalkyl, and wherein one or more carbon atoms in said 3 groups is optionally replaced with a heteromoiety selected from O, S, N, NH or $N(C_1-C_6)$-alkyl;
$R^2$, $R^3$, $R^{2'}$ and $R^{3'}$ are independently $(C_1-C_{10})$-alkyl, $(C_2-C_{10})$-alkenyl or $(C_2-C_{10})$-alkynyl all 3 groups optionally substituted by one or more groups selected from halo, $OR^5$ or $R^5$, in which $R^5$ is selected from $(C_1-C_6)$-alkyl, $(C_2-C_6)$-alkenyl, $(C_2-C_6)$-alkynyl or $(C_3-C_6)$-cycloalkyl;
Sp is a spacer moiety bonded to the linker moiety L; and
X is any suitable anionic counterion.

In one embodiment of the disclosure, $R^1$ and $R^{1'}$ are independently or simultaneously $(C_{10}-C_{22})$-alkyl, $(C_{10}-C_{22})$-alkenyl, $(C_{10}-C_{22})$-alkynyl or $(C_6-C_{10})$-aryl. In another embodiment, $R^1$ and $R^{1'}$ are independently or simultaneously $(C_{10}-C_{12})$-alkyl, $(C_{10}-C_{12})$-alkenyl or $(C_{10}-C_{12})$-alkynyl. In another embodiment, $R^1$ and $R^{1'}$ are $C_{12}$-alkyl.

In another embodiment, $R^2$, $R^3$, $R^{2'}$ and $R^{3'}$ are independently or simultaneously $(C_1-C_6)$-alkyl, $(C_2-C_6)$-alkenyl or $(C_2-C_6)$-alkynylene. In a further embodiment, $R^2$, $R^3$, $R^{2'}$ and $R^{3'}$ are independently or simultaneously $(C_1-C_3)$-alkyl, $(C_2-C_3)$-alkenyl or $(C_2-C_3)$-alkynylene. In a further embodiment, $R^2$, $R^3$, $R^{2'}$ and $R^{3'}$ are independently or simultaneously methyl, ethyl, propyl or iso-propyl. In a further embodiment, $R^2$, $R^3$, $R^{2'}$ and $R^{3'}$ are methyl.

In another embodiment of the disclosure, the spacer moiety Sp is $(C_1-C_{10})$-alkylene, $(C_2-C_{20})$-alkenylene, $(C_2-C_{20})$-alkynylene, $(C_3-C_{10})$-cycloalkylene, or any combination thereof, wherein said 4 groups are optionally substituted by one or more groups selected from halo, $OR^5$ or $R^5$, in which $R^5$ is selected from $(C_1-C_6)$-alkyl, $(C_2-C_6)$-alkenyl, $(C_2-C_6)$-alkynyl or $(C_3-C_6)$-cycloalkyl, and wherein one or more carbon atoms in said 4 groups is optionally replaced with a heteromoiety selected from O, S, N, NH or $N(C_1-C_6)$-alkyl. In a further embodiment, the spacer moiety Sp is $(C_1-C_{10})$-alkylene, $(C_2-C_{10})$-alkenylene, $(C_2-C_{10})$-alkynylene, $(C_3-C_6)$-cycloalkylene, or any combination thereof. In another embodiment, the spacer moiety Sp is $(C_1-C_8)$-alkylene, wherein one or more carbon atoms in said group is optionally replaced with a heteromoiety selected from O, S, N, NH or $N(C_1-C_6)$-alkyl. In another embodiment, the spacer moiety is a $C_7$-alkylene moiety, wherein one or more carbon atoms is optionally replaced with a nitrogen atom.

In another embodiment, the spacer moiety Sp is

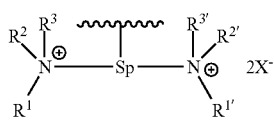

In another embodiment of the disclosure, $X^-$ is a halogen ion.

In an embodiment of the disclosure, the gemini surfactant moiety is

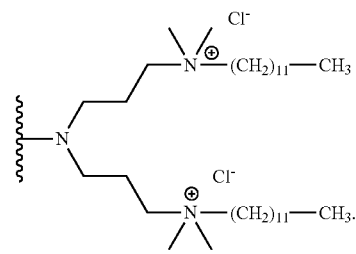

In an embodiment of the disclosure, the cyclodextrin moiety, or derivative thereof, is a moiety of α-cyclodextrin, β-cyclodextrin or γ-cyclodextrin. In another embodiment, the cyclodextrin moiety is a β-cyclodextrin moiety, or a derivative thereof.

In one embodiment, compounds of the formula (I) are in the form of nanoparticles having a diameter of between 100 nm to 500 nm, optionally 125 nm to 250 nm, or 140 nm to 160 nm, or about 150 nm. Without being bound by theory, the nanoparticulate nature of the delivery agent facilitate active cellular uptake,[14] and therefore aids in the delivery of the therapeutic agent to where it is needed. In addition, in one embodiment, nanoparticles consisting of compounds of the formula (I), wherein the therapeutic agent is an anticancer agent, have the ability overcome drug resistance often associated with conventional naked drug molecules.[15]

In one embodiment, the gemini surfactant moieties conjugated to the cyclodextrin moieties of the compounds of formula (I) self-assemble into cationic nanoparticles and act as efficient in vivo cutaneous permeation enhancers for therapeutic agents. Without being bound by theory, the gemini surfactant moieties demonstrate lower cellular toxicity,[5] higher efficiency in reducing surface tension, and greater tendency to self-assemble compared to monovalent permeation enhancers.[6]

In one embodiment, the nanoparticles further comprise a therapeutic agent as defined above which complexes with the cyclodextrin moiety.

(IV) Methods of Medical Treatment

The present disclosure also includes methods of medical treatment comprising the administration of the pharmaceutical composition or pharmaceutical nanoparticles to a mammal. In one embodiment, the pharmaceutical composition or pharmaceutical nanoparticles are formulated to be suitable for the topical administration of a skin disorder, such as skin cancer (melanoma) or dermatoses requiring pharmacotherapy.

Also included in the present disclosure is a method for the treatment of melanoma in a mammal, comprising topically administering to the mammal a therapeutically effective amount of a composition or nanoparticle as defined above, and wherein the therapeutic agent is an anti-neoplastic agent. In another embodiment, the mammal is a human.

In another embodiment, the present disclosure also includes a method for inhibiting the growth of a melanoma cell, comprising contacting the melanoma cell with a therapeutically effective amount of a composition or nanoparticle as defined above, and wherein the therapeutic agent is an anti-neoplastic agent. In one embodiment, the therapeutic agent (i) encapsulated in formula (I) is applied on the surface of the skin. Pharmacokinetic assessment (absorption into the tissue, half-life and elimination) in conjunction with the effective inhibitory concentration ($IC_{50}$) aids to determine the dose, dosing interval and length of therapy. In addition, the stage of the melanoma (spread of the disease) will also determine the extent of the therapy.

In another embodiment, the compositions and/or nanoparticles are suitable for mucosal (nasal, rectal, vaginal or buccal) administration for the delivery of therapeutic agents to treat affected melanocytes in the oral mucosa and in the eye (oral and uveal). In another embodiment, the compositions and/or nanoparticles are suitable for parenteral (intravenous and subcutaneous) administration for the delivery of therapeutic agents to treat metastatic melanoma. In another embodiment, the compositions and/or nanoparticles are suitable for the oral administration of anti-depressant medications or anti-retroviral medications. The compositions of the disclosure are also suitable for cosmeceutical delivery, and can therefore be combined with cosmetically acceptable carriers, excipients, and/or vehicles.

In other embodiments, the pharmaceutical compositions are suitable for veterinary use, such that the drug delivery agent is useful for the delivery of a therapeutic agent to an animal.

The dosage of the pharmaceutical compositions or nanoparticles can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I). A low µM $IC_{50}$, as demonstrated for the therapeutic agent (i), is required for the development of effective antineoplastic therapy.

In one embodiment, the pharmaceutical compositions or nanoparticles of the present disclosure wherein the therapeutic agent comprises an antineoplastic agent inhibit the growth of tumor cells by arresting cellular proliferation and inducing apoptosis. Apoptosis can be activated in the cell by changing regulation pathways, thus the cell undergoes a programmed cell death without damaging healthy neighbouring cells. However, tumor cells can circumvent the apoptotic pathway allowing the damaged genetic code to replicate. Curcumin, as an example of an anti-neoplastic therapeutic agent, overrides cellular replication by causing the human melanoma cells to self-destruct by a Fas receptor/caspase-8 pathway.[16]

Although the disclosure has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present disclosure.

EXAMPLES

The operation of the disclosure is illustrated by the following representative examples. As is apparent to those skilled in the art, many of the details of the examples may be changed while still practicing the disclosure described herein.

Materials and Methods

The 1,5-diaryl-3-oxo-1,4-pentadienyl derivatives NC2067 and NC2081 were synthesized as described.[4]

Unless otherwise stated, all reactions were performed under a $N_2$ atmosphere using standard Schlenk techniques. $^1H$ and $^{13}C$ NMR spectra were recorded on a Bruker 500 MHz Avance spectrometer. Chemical shifts for $^1H$ NMR and $^{13}C$ NMR are reported in ppm in reference to the residual 1H and $^{13}C$ resonances of $CDCl_3$ (δ 7.26, 77.22, respectively) and DMSO-$d_6$ (δ 2.50). Mass spectra were obtained using an Applied Biosystem QSTAR®XL MS/MS System (ESI-Q-TOF). The reagents, 3,3'-iminobis(N,N-dimethyl-propylamine), succinic anhydride, 1-iodododecane, N,N'-dicyclohexylcarbodiimide (DCC), dimethylformamide (DMF, dried and kept under molecular sieves), 4-dimethylaminopyridine (DMAP) and Amberlite®IRA-400(Cl) ion exchange resin were purchased from Sigma-Aldrich and were used as received. β-Cyclodextrin, dried before use, was purchased from Alfa Aesar, while 1-hydroxy-benzotriazole (HOBt, Matrix Innovations) was used as received. Statistical analysis was performed using PASW Statistics 18 software. Samples were analyzed using one-way analysis of variance and Tukeys multiple comparison. The level of significance was set to $p<0.05$.

Cells

A375, human amelanotic melanoma cells (American Type Culture Collection CRL-1619), were grown in Dulbecco's modified Eagle's medium (DMEM, Gibco) supplemented with 10% fetal bovine serum (FBS, Gibco), 100 U/mL penicillin, 100 µg/mL streptomycin and 25 ng/mL amphotericin B (Sigma). HEKa, normal adult human epidermal keratinocyte cells (Cascade Biologics, Invitrogen), were grown in Medium 154 (Gibco) supplemented with Human Keratinocyte Growth Supplement (HKGS, Gibco) and 100 U/mL penicillin, 100 µg/mL streptomycin and 25 ng/mL amphotericin B. Both cell lines were cultured at 37° C. in a humidified incubator with 5% $CO_2$ and 95% air. For all experiments, passage numbers and incubation times were kept consistent. All cell culture ware was purchased from BD Biosciences.

Example 1

Synthesis of the cyclodextrin-gemini agent [mono-6-o-3{bis(3-(N-dodecyl-N,N-dimethylamino) propylcarbamoyl}propanoyl)-beta-cyclodextrin]$^{2+}$ Step a: Synthesis of bis(3-(N,N-dimethylaminopropyl)carbamoyl) propanoic acid A Schlenk flask, equipped with a magnetic stir bar, was charged with 3,3'-iminobis(N,N-dimethyl-propylamine) (1.682 g, 8.989 mmol) and succinic anhydride (0.988 g, 9.873 mmol) in 15 mL of DMF to form a homogeneous solution. After 3 d of stirring at ambient temperature, the reaction mixture was concentrated under vacuum to obtain an orange-yellow oily substance as the desired compound in quantitative yield. $^1$H NMR (500 MHz, $CDCl_3$): δ 13.29 (s, 1H, $CO_2$H), 3.29 (t, 4H), 2.52 (m, 4H), 2.46 (t, 2H), 2.37 (t, 2H), 2.32 (s, 6H, $NMe_2$) 2.26 (s, 6H, $NMe_2$), 1.73 (m, 4H). $^{13}$C NMR (500 MHz, $CDCl_3$): δ 178.00, 172.72, 56.18, 56.05, 45.88, 44.69, 44.18, 43.68, 31.55, 29.08, 26.39, 24.80.

Step b (i,ii): Synthesis of [3-{bis(3-(N-dodecyl-N,N-dimethylamino)propyl) carbamoyl}propanoic acid]$^{2+}$ A round-bottom flask was charged with the product from step a, 3-(bis(3-(N,N-dimethylamino)propyl)carbamoyl) propanoic acid, (800.0 mg, 2.785 mmol) and 1-iodododecane (2.063 g, 1.720 mL, 6.933 mmol) in DMF (20 mL) to form a yellow homogeneous solution. After 12 h of stirring at ambient temperature, the solvent was removed under vacuum and the residue washed several times with diethyl ether to remove the excess iodododecane. The sample was dried yielding an orange oily substance that was dissolved in 10 mL of distilled water and 2.5 equivalents of Amberlite® IRA-400(Cl) (2.400 g, 6.933 mmol) was added to the solution. After stirring for 1 h, Amberlite resin was removed by filtration and washed with water. An orange, oily substance was obtained in almost quantitative yield after removing excess water by freeze-drying. $^1$H NMR (500 MHz, $CDCl_3$) δ 3.62 (m, 2H), 3.54 (m, 4H), 3.43-3.34 (m, 6H), 3.18 (s, 6H, $NMe_2$), 3.13 (s, 6H, $NMe_2$), 2.74-2.67 (m, 4H), 2.20 (m, 2H), 2.62 (m, 2H), 1.81 (m, 4H), 1.41-1.30 (m, 36H), 0.90 (t, 6H). ESI-MS m/z calculated for $C_{38}H_{79}N_3O_3{}^{2+}$; 312.8063 [M-2Cl]$^{2+}$. found 312.7 [M-2Cl]$^{2+}$.

Step c: Synthesis of [mono-6-o-(3{bis(3-(N-dodecyl-N,N-dimethylamino)-propyl)-carbamoyl}propanoyl)-beta-cyclodextrin]$^{2+}$ A Schlenk flask was charged with the gemini-linker compound obtained in step b, [3{bis(3-(N-dodecyl-N-dimethylamino)propyl)carbamoyl}propanoic acid]$^{2+}$, (188.1 mg, 0.2699 mmol) and β-cyclodextrin (158.7 mg, 0.1398 mmol), HOBt (44.00 mg, 0.3239 mmol) and DMAP (3.300 mg, 0.0270 mmol) were added sequentially to 10 mL of dry DMF. The mixture was cooled to below 0° C. before the addition of solid DCC (66.80 mg, 0.3239 mmol). The homogeneous mixture was allowed to warm to room temp and stirred, overnight, then heated to 50° C. for 48 h. Upon cooling, a precipitate formed, which was isolated and washed with acetone (3×20 mL). To the concentrated filtrate, excess acetone was added to precipitate a white powder, which was washed with acetone and dried to obtain the desired compound (165.0 mg, 65% yield). The analytical and spectral data were in agreement with the proposed structure. $^1$H NMR (DMSO-$d_6$) showed a down field shift of the protons ($O_6$H) at the primary face of the CD. The integrated intensity showed ca. 1/7 decrease indicating that this was the OH to which the tethered-gemini was attached. The ESI-MS spectrum shows a peak at m/e 870.9968 [M-2Cl]$^{2+}$, which is the mass for a doubly charged species of the proposed structure. H$^1$ NMR (500 MHz) DMSO: δ 5.75 (d, 7H, $O_2$H), 5.71 (s, 7H, $O_3$H), 4.83 (s, 7H, $C_1$), 4.54-4.48 (m, 6H, $O_6$H), 3.65-3.54 (m, 30H), 3.37-3.25 (m, 24H), 3.05-2.98 (m, 12H, $NMe_4$), 2.63-2.59 (m, 4H), 1.98-1.88 (m, 4H), 1.64 (m, 4H), 1.23 (br s, 36H), 0.86 (t, 6H, Me). ESI-MS m/z calculated for $C_{80}H_{147}N_3O_{372}{}^{2+}$; 870.9851 [M-2Cl]$^{2+}$. found; 870.9968 [M-2Cl]$^{2+}$.

Example 2

UV Analysis to Assess Stoichiometry of the Drug/CD and drug/CDgemini Complexes

The UV absorption of the composition was measured at 335 nm using a Synergy plate reader (BioTek, USA). The experiment was repeated three times. NC 2067 was dissolved in water to a final concentration of 100 µM. On a 96-well plate, increasing amounts of CD or CDgemini in the concentration range of 10-400 µM was added to the drug in quadruplicate wells. The formulations were incubated for 1 h in the dark at room temperature prior to measuring the UV spectrum.

Discussion

In order to determine the approximate stoichiometry of the drug/CD and drug/CDgemini complexes, NC 2067 was used for this assessment because of its solubility in water (approx 300 µM) compared to the NC 2081 (10 µM). The absorbance of the drug showed only a very slight decrease in the presence of increasing concentration of CD while in the presence of the CDgemini a much steeper, linear decrease in absorbance was observed until the CDgemini to drug mole ratio reached a value of 2. Thereafter, the absorbance remained constant upon further addition of drug (as shown in FIG. 1). The 2:1 molar ratio was used in subsequent formulations for the cytotoxicity assays.

Based on the change in absorbance of NC 2067 in the presence of the CDgemini, the evidence of the drug/CD conjugate in the MS analysis and the nanoparticulate nature (evidenced by dynamic light scattering and TEM), a schematic model for the potential interaction of the drug with the delivery agent (as shown in Scheme 1).

Scheme 1
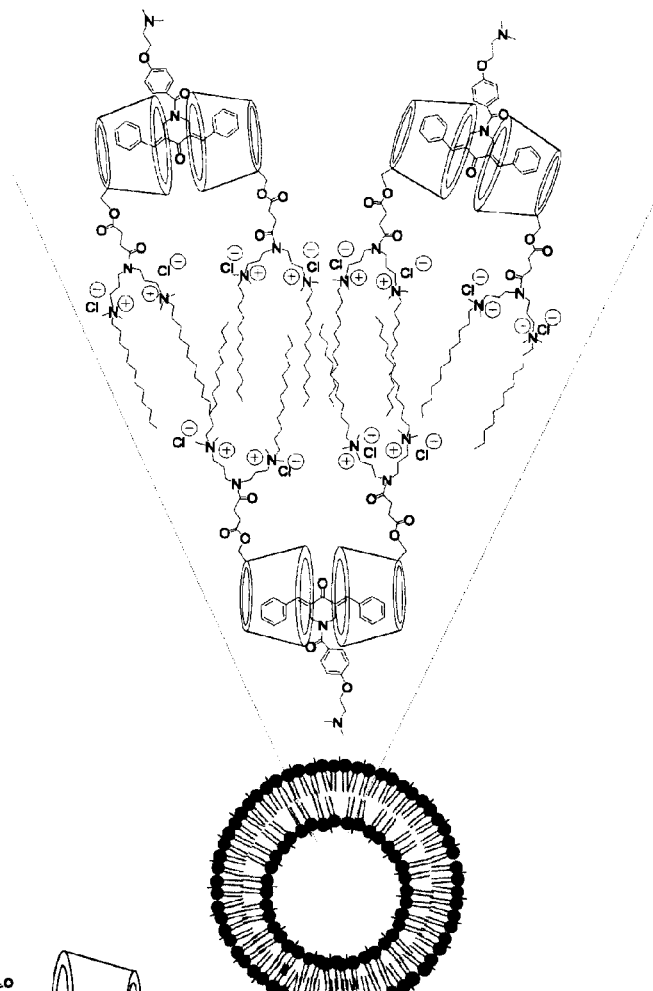
Scheme 2
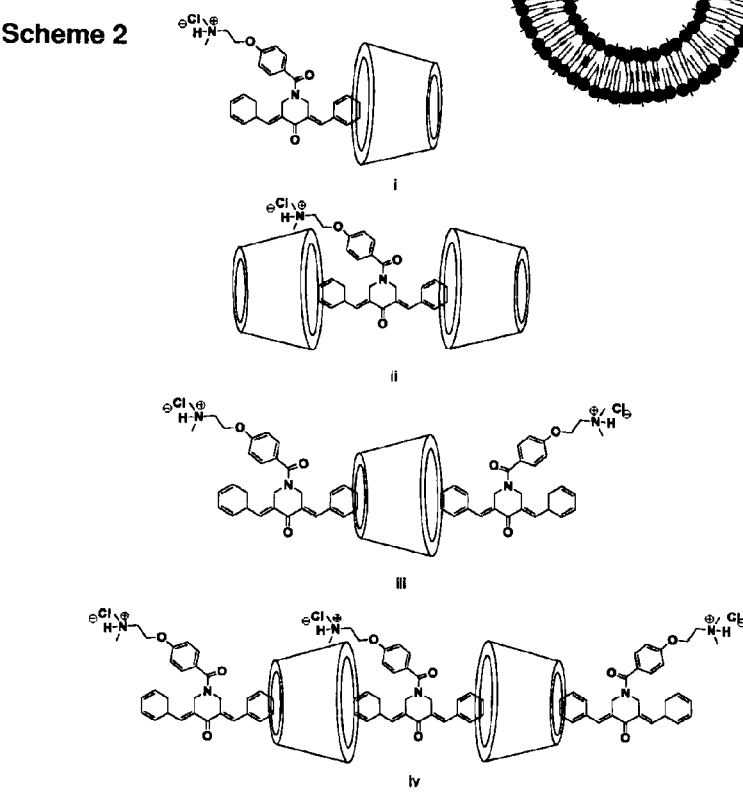

In this embodiment, the alkyl tails of the gemini surfactant of the CDgemini result in the molecules forming a bilayer-type of assembly. The exposed CD rings on the bilayer surface can incorporate one of the aromatic rings of the drug molecule, requiring two CDgemini molecules for each drug molecule (Scheme 2). Without being bound by theory, it is thought that this is why there is very little change in the UV absorbance of the drug in the presence of CD alone: there is no organization of the CD rings in the aqueous media due to a lack of hydrophobic gemini tails inducing self-assembly by means of hydrophobic interactions. The absence of an organized structure in aqueous media precludes the drug from inserting into the CD cavity but the drug can randomly interact with the CD through much weaker facial interaction.

Example 3

Preparation of Pharmaceutical Compositions

Due to their low solubility in water, for the in vitro testing, each drug was dissolved in dimethylsulfoxide (DMSO, Sigma) at 2 mM concentration. The drug was added at increasing concentrations of 0.01-200 µM to the supplemented media with the final DMSO concentration of 2% exposed to the cells. For the formulations, CD or CDgemini was dissolved in water (10 mM) and the drugs were dissolved in methanol (2 mM). The delivery agent to drug mole ratio was maintained at 2:1. The solvent mixture was evaporated in a rotary evaporator under vacuum and the residue was reconstituted in water. Samples were dispersed by sonication for 2 h and stored overnight at 4° C. Samples were re-sonicated, prior to diluting in supplemented media, for 15 min.

Example 4

Size and ζ-Potential Measurement of Compositions

Figure 3:
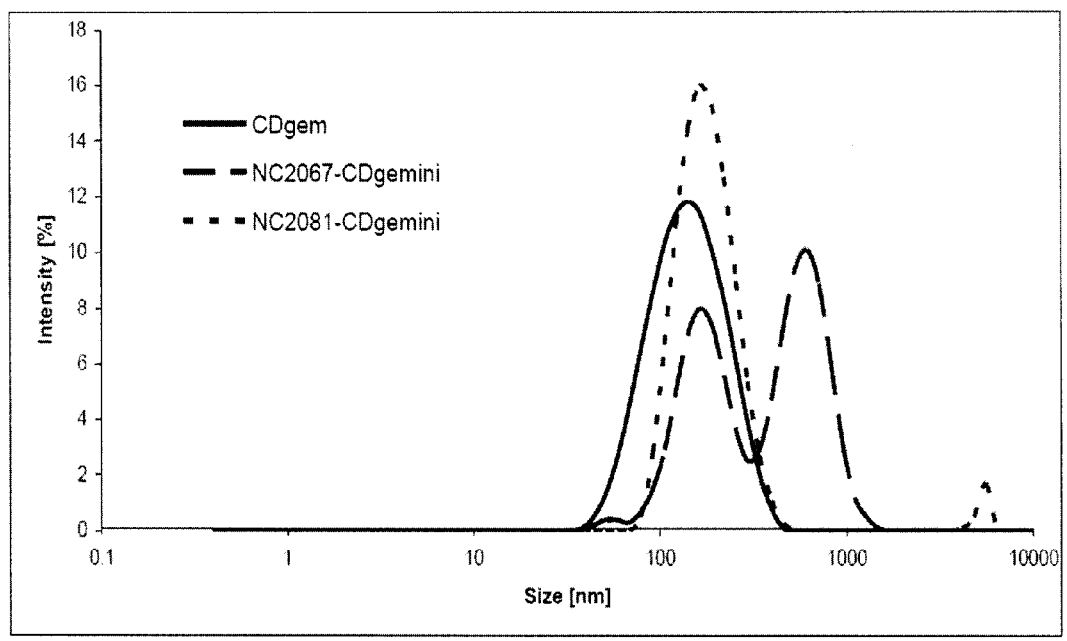
FIG. 3 is a graph showing the size distribution, in one embodiment, of a CDgemini or a therapeutic agent/CDgemini conjugate.

Compositions were prepared as described above. The size and ζ-potential of the particles were measured with a Zetasizer Nano ZS instrument (Malvern Instruments, UK). Results are reported as the mean of 3-5 measurements±standard deviations.
Discussion
To further evaluate the aggregation behaviour of the CD and CDgemini agents in conjunction with the drugs, particle size and ζ-potential measurements were carried out. It was observed that neither CD nor drug/CD conjugates formed supramolecular aggregates. The CDgemini compound formed nanoparticles of 153.6±4.3 nm (as shown in FIG. 3). In the drug/CDgemini system, the particle size increased to 173.2±24 for NC 2067 and 185±17.5 for NC 2081, respectively (see Table 1). The NC 2067/CDgemini formulation showed another peak indicating larger particles (600 nm diameter) that might be aggregates of the nanoparticles, also suggested by the high polydispersity index (PDI).

The ζ-potential was positive, 5.74±0.53, but relatively low for the CDgemini alone and increased significantly in the drug/CDgemini complexes to over 40 mV.

Example 5

Transmission Electron Microscopy (TEM) of Compositions

Figure 4:
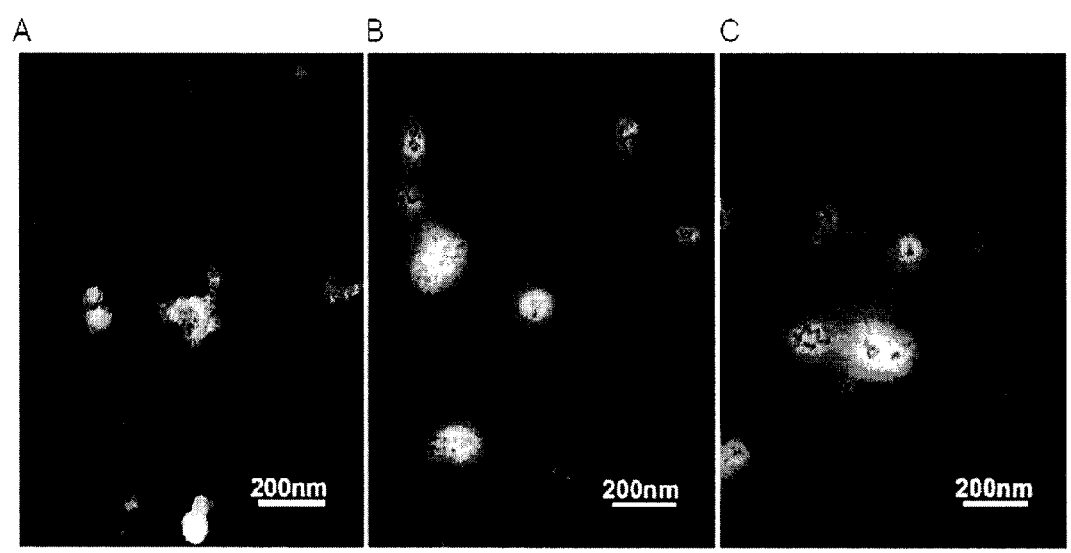
FIG. 4 shows transmission electron micrographs, in an embodiment of the disclosure, of a CDgemini complex (A), a therapeutic agent/CDgemini composition (B) and a therapeutic agent/CDgemini (C) composition.

Drug/CDgemini conjugates prepared for the size measurements were used for TEM. Aliquots of 10 µL samples were dropped onto 300-mesh formvar-coated copper grids (SPI Supplies) and incubated for 5 min at room temperature. The water was wicked off the grids with absorbent tissue and the grids were stained with 1% phosphotungstic acid for 2 min. The stain was removed and the grids were dried at room temperature for 15 min. The samples were examined with a Philips CM10 electron microscope at an accelerating voltage of 80 kV.
Discussion
TEM images of the CDgemini particles (shown in FIG. 4A) showed the size being 100-150 nm and revealed a vesicular nature. The formulations with the drugs (see FIGS. 4B and C) appear smaller than those measured by light scattering, which may due to the drug forming crystals in the drying process. The granular nature of the particles also suggests crystallization.

Example 6

Mass Spectrometry of Compositions

The drugs, CD and CDgemini were tested by MS techniques to confirm their molecular structure and complexation of the drug with the delivery system.

A hybrid Triple Quadrupole/Linear Ion trap mass spectrometer (AB Sciex 4000 QTRAP MS/MS system, US) fitted with an electrospray ionization (ESI) source was used for single-stage MS as well as MS/MS analysis. The instrument was operated in the positive ion mode with the following parameters: declustering potential 186 V, entrance potential 10 V, ionspray voltage 4500 V and temperature of 500° C. The drug/CD and drug/CDgemini formulations were infused into the mass spectrometer to assess complex formation. Each composition was diluted to 20 µM CD or CDgemini and 10 µM of drug in methanol, prior to injecting into the mass spectrometer.

Figure 2A:
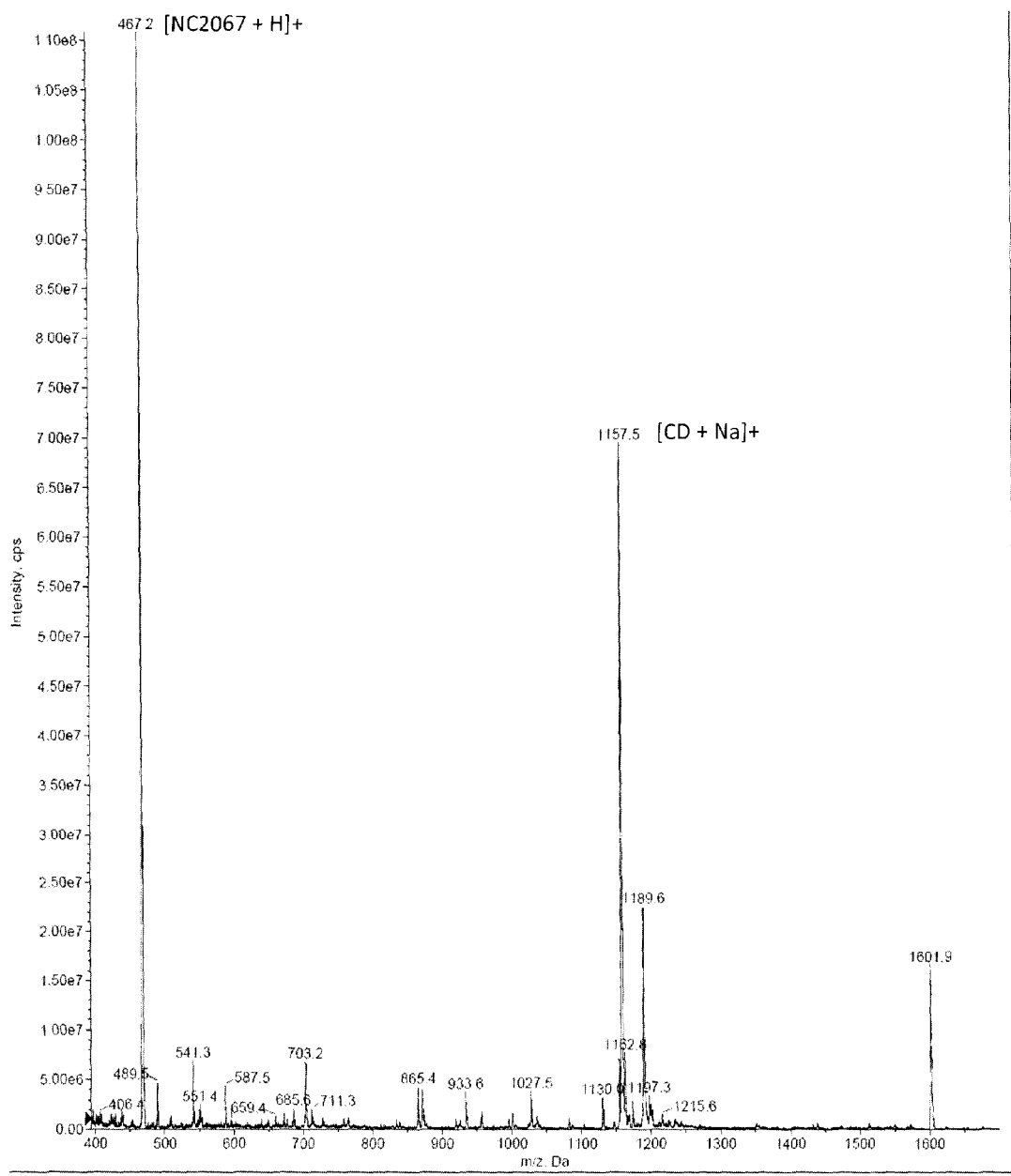
FIG. 2 shows a mass spectra of a therapeutic agent in a CD complex in an embodiment of the disclosure.
Figure 2B:
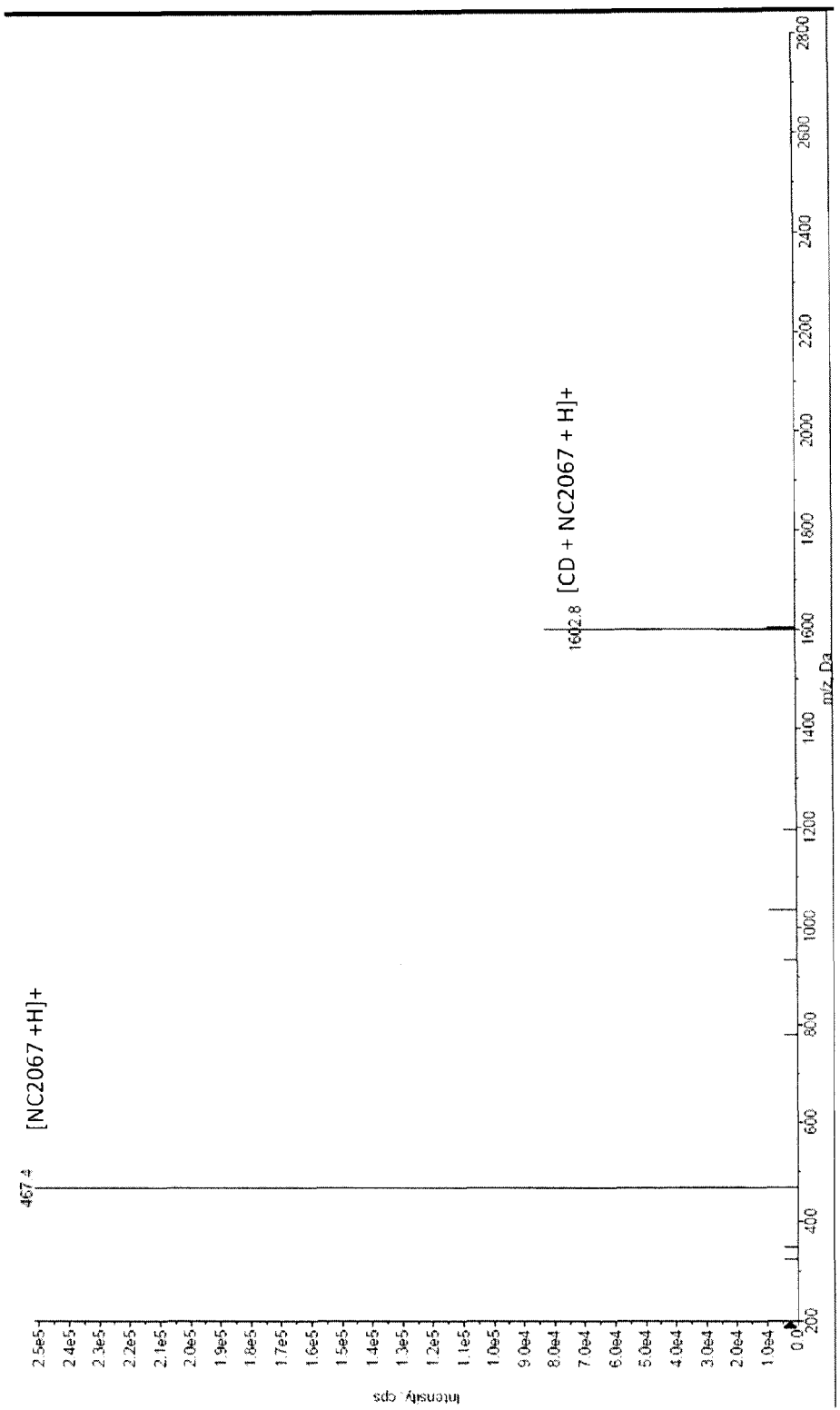

Collisionally activated dissociation (CAD) tandem MS analysis of gemini surfactants and Drug/CD were performed using the 4000 QTRAP system. All parameters utilized during MS analysis were maintained for MS/MS analysis. Nitrogen was used as the collision gas the collision energy was optimized at 53 V and CXP 10 V for each. The collision energy optimization was performed in order to ensure the formation of fragment ions while maintaining the presence of the precursor ion.
Discussion
Single-stage ESI-MS analysis of the drug/CD complex was performed at a stoichiometric molar ratio of CD to drug of 2 (see FIG. 2). The following ions were observed at m/z=1602 representing the drug/CD complex and was designated as $[CD+NC\ 2067+H]^+$ and m/z=467 the protonated form of the antineoplastic drug moiety $[NC\ 2067+H]^+$. In addition, sodiated adduct of the CD was observed at m/z 1157 $[CD+Na]^+$.

MS/MS analysis of $[CD+NC\ 2067+H]^+$ resulted in the formation of the product ion m/z 467 representing $[NC\ 2067+H]^+$ with a neutral elimination of the CD moiety, demonstrating the association between CD and the NC 2067. It should be noted that CD was only observed as a sodiated adduct regardless of the experimental conditions during single stage MS; therefore, it cannot be observed during MS/MS of $[CD+NC\ 2067+H]^+$ since the selected ion does not carry a sodium into the collision cell.

Example 7

Cell Toxicity and Assay

Both A375 and HEKa cells, at the second passage, were seeded at a density of $1 \times 10^4$ and $2.5 \times 10^5$ cells per well, respectively, in 96-well tissue culture-treated plates. Cells were incubated at 37° C. in a humidified incubator with 5% $CO_2$ for 24 h. The medium was changed with supplemented media containing different concentrations of compositions (0.01-200 µM) and controls (including the 2% DMSO, 14 µM CD, 14 µM CDgemini). Cells were treated in quadruplicate wells for 48 h to produce a balanced 4-parameter curve. The experiment was conducted in triplicate for both cell lines at the same passage number.

After treatment, fresh supplemented media containing a final concentration of 450 µg/mL 3-(4,5-dimethylthiazol-2-yl)-2,5-diphenyltetrazolium bromide (MTT, Invitrogen) solution was added to each well and the plates was incubated for 2 h at 37° C. Excess MTT solution was removed and the plates were dried. DMSO was added to each well and the plates were incubated for 10 min at 37° C. to dissolve the trapped formazan. Absorbance at 550 nm was recorded using a Synergy BioTek plate reader. The fraction of dead cells was calculated as $$\text{Fraction of dead cells} = \frac{Abs_{control} - Abs_{treated}}{Abs_{control}}$$

The $IC_{50}$ values for all samples were calculated using the 4-parameter curve generated by the GEN5 software from BioTek.

Discussion

The therapeutic agents (NC-2067 and NC-2081) dissolved in DMSO and incorporated in compositions induced strong cytotoxic effects in A375 cells (see Table 2). The $IC_{50}$ values of the NC 2067 and NC 2081 in DMSO were 0.47±0.03 µM and 0.93±0.03 µM, respectively. The performance of the two drugs in DMSO was not significantly different (p>0.05). The drug/CD and drug/CDgemini compositions of the NC 2067 were slightly less toxic than the DMSO solutions, the $IC_{50}$ values for the treated cells being 0.80±0.06 µM and 0.86±0.07 µM, respectively, but not significantly different from DMSO (p>0.05).

Figure 5:
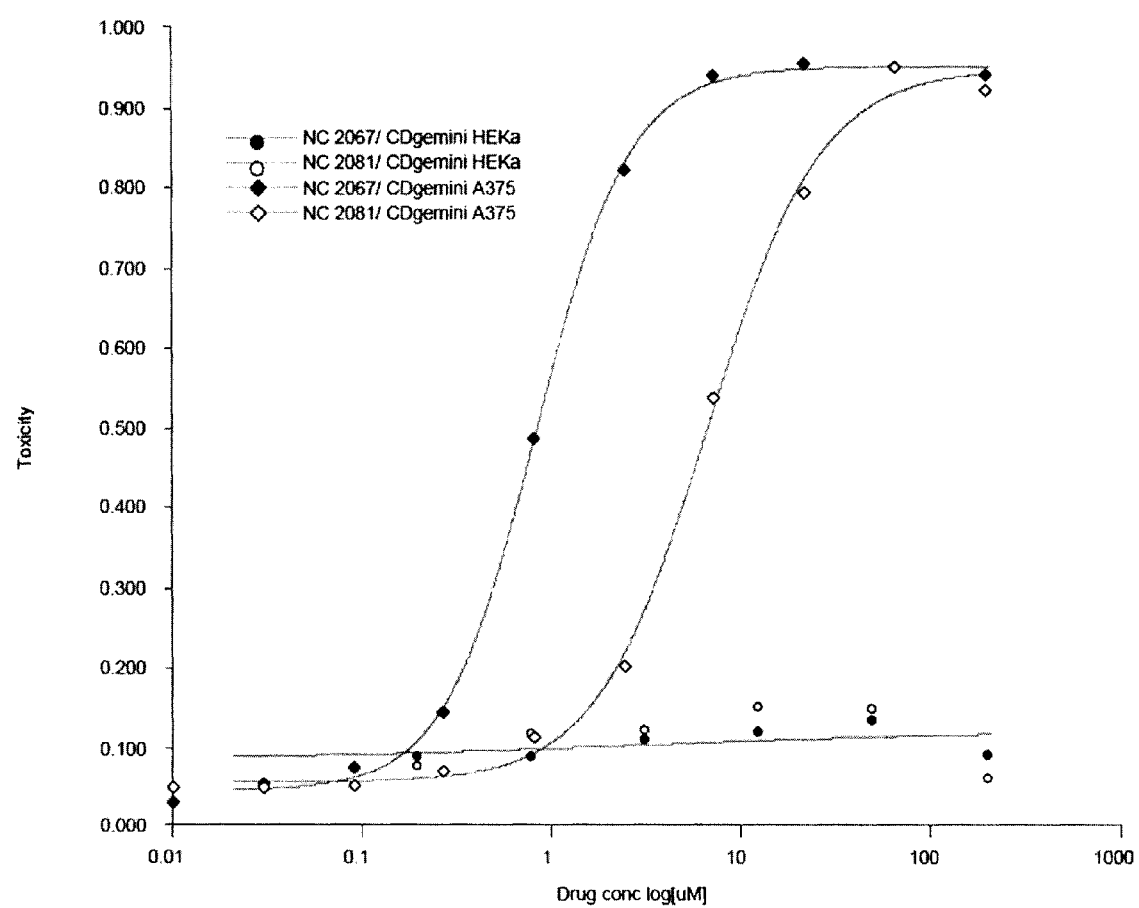
FIG. 5 is a graph showing the toxicity of a composition of the disclosure in A375 and HEKa cell lines.
Figure 6A:
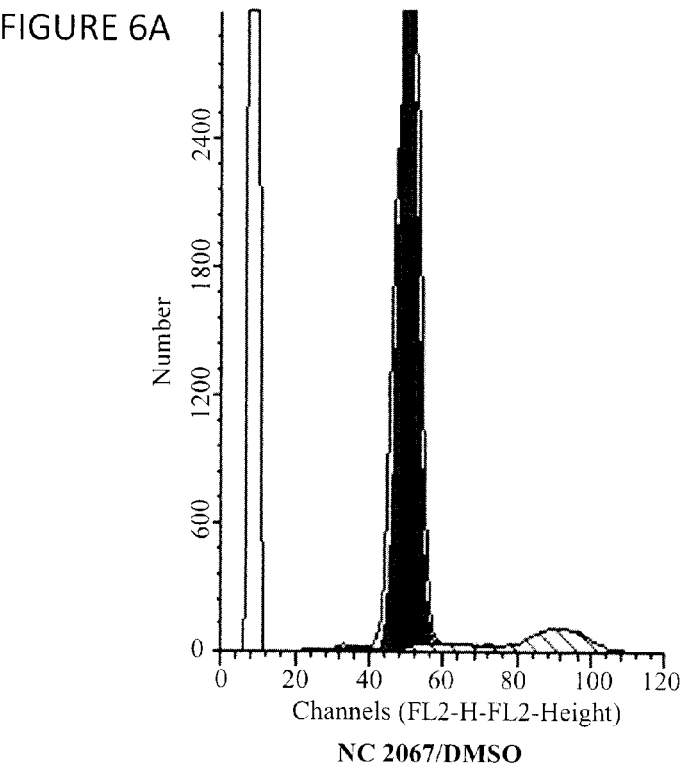
FIG. 6 shows the effect of compositions of the disclosure on A375 cell cycle represented as percentage of total cell population.
Figure 6A:
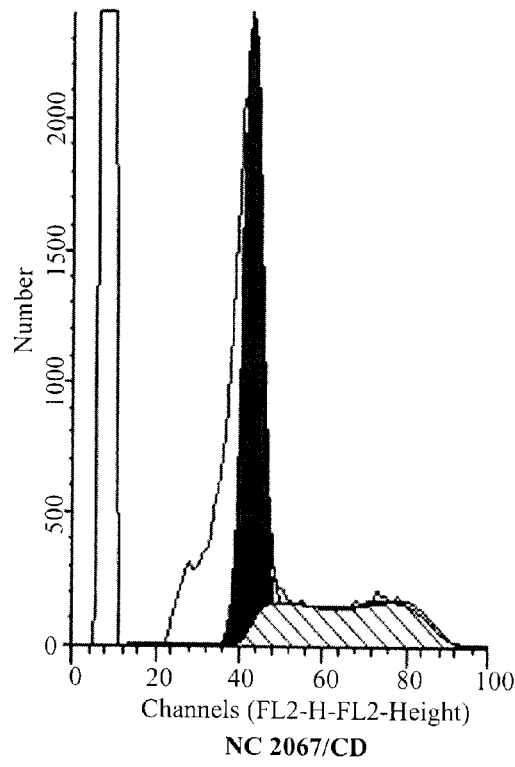
Figure 6A:
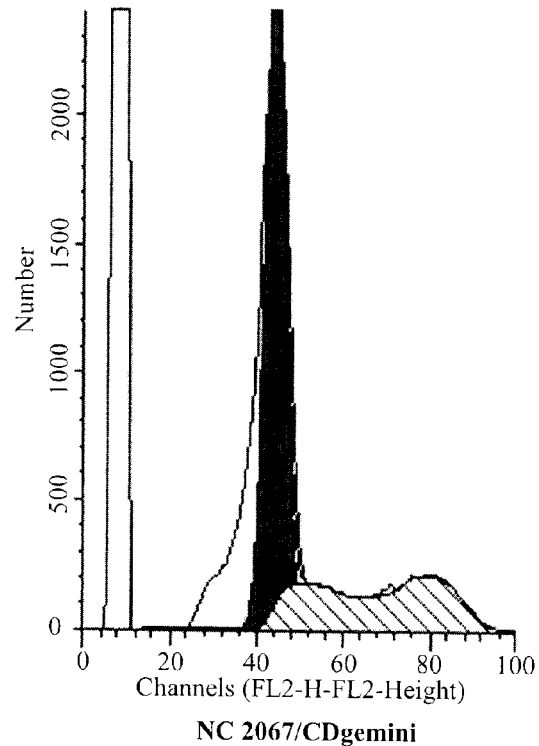
Figure 6B:
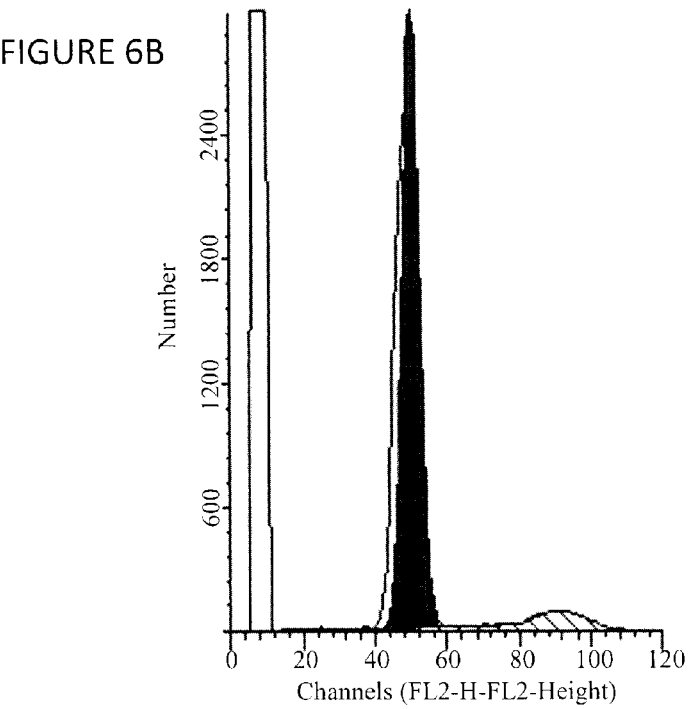
Figure 6B:
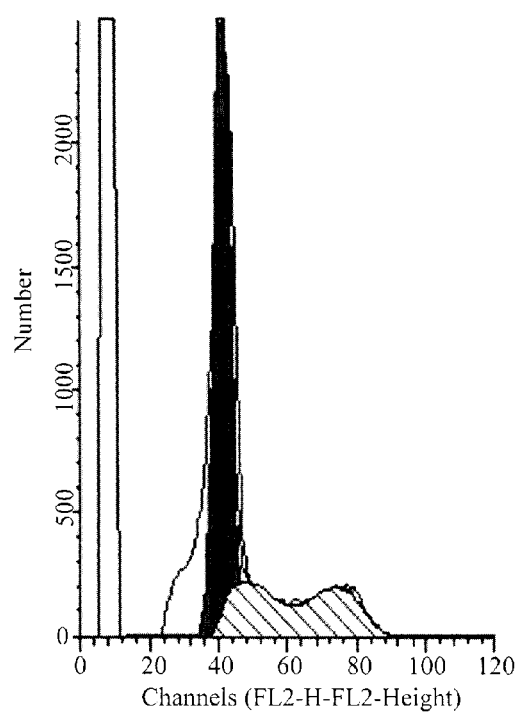
Figure 6B:
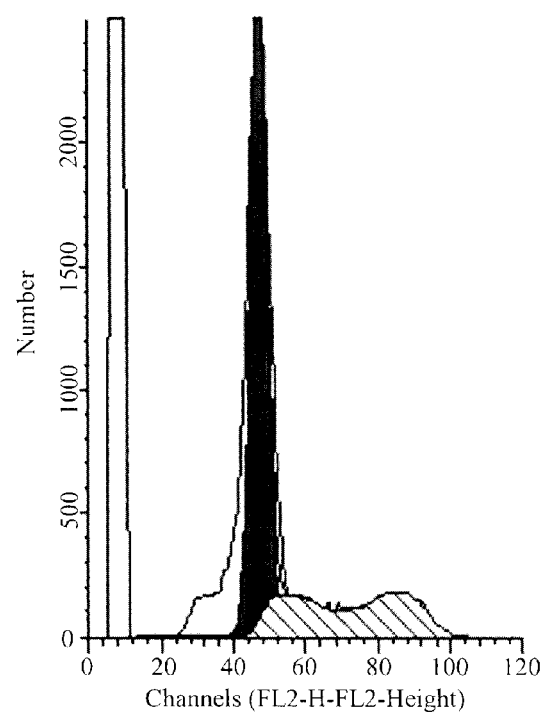
Figure 6C:
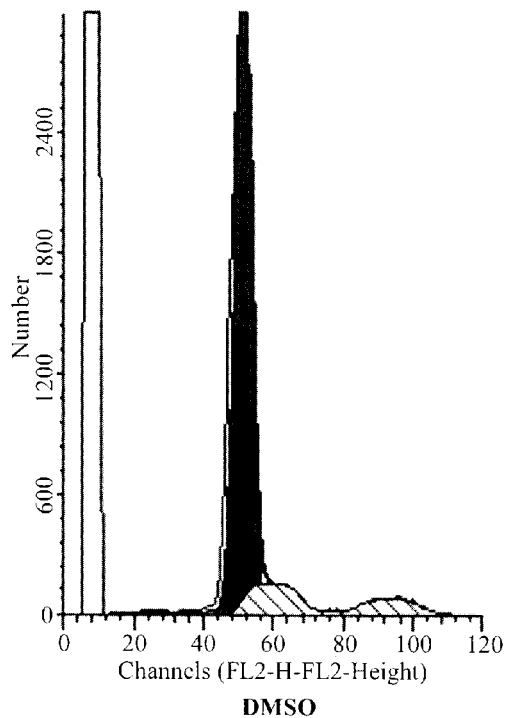
Figure 6C:
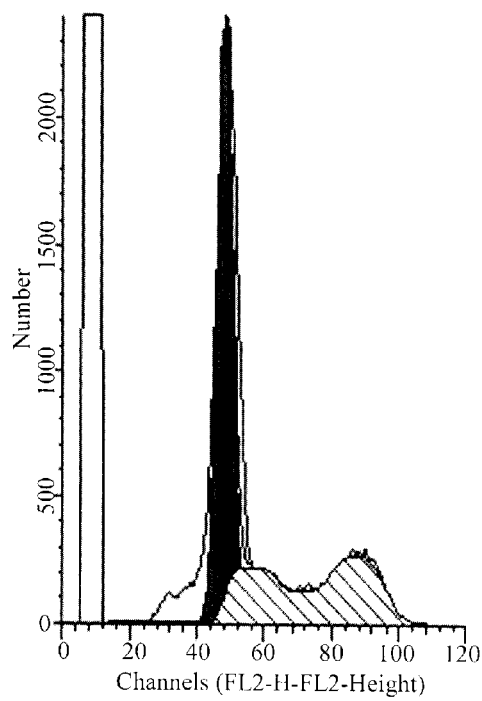
Figure 6C:
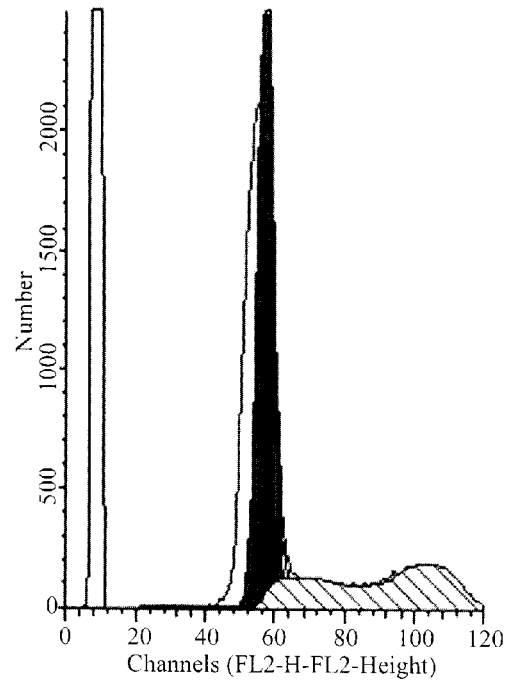

The effect of the drug/CDgemini formulations in HEKa to A375 cell lines was compared (as shown in FIG. 5). There was only about 10% cellular death in the HEKa cells at 1-10 µM drug concentrations (around the $IC_{50}$ in the A375) and less than 15% at 200 µM concentration, indicating a 20-200-fold higher toxicity of the composition to the cancer cells.

The cytotoxic concentrations of the drug/CD and drug/CDgemini formulations (1-8 µM) are significantly lower compared to melphalan, the currently used drug for in-transit melanoma limb perfusion,[17] namely 52-219 µM in a number of cancer cells, including human SK-MEL-5 cells.[18]

Example 8

Flow Cytometry

A375 cells at the second passage were seeded at a density of $1 \times 10^6$ cells per well in 6 well tissue culture-treated plates. Cells were incubated at 37° C. in a humidified incubator with 5% $CO_2$ and 95% air, overnight. The medium was changed with supplemented media containing the formulations at $IC_{50}$ concentrations and controls including 2% DMSO, 14 µM CD, 14 µM CDgemini, 30 µM resveratrol (Sigma), 2 mM sodium butyrate (Sigma) and supplemented DMEM. The resveratrol and sodium butyrate controls were used to calibrate the flow cytometer for cell cycle arrest in the A375 cell. All treatments were performed in triplicate wells. Cells were incubated with the formulations and controls for 48 h. All cells, floating and adherent, were collected, the triplicate wells pooled and washed in PBS. The cell populations were divided into two. Half of the cells was fixed in 70% ethanol for 2 h, washed twice in 300 µg/mL RNase A (Qiagen) in PBS. The cell pellet was resuspended in PBS and stained with propidium iodide, 20 µg/mL (Sigma). The other half of the cells was suspended in binding buffer and stained as per the Annexin V-FITC Apoptosis Detection Kit (BioVision) protocol.

Flow cytometry was performed with a FacsCalibur instrument (BD Biosciences). The treatment groups were analyzed using ModFit LT flow cytometry modeling software (Verity Software House, Inc) after gating the area of non-treated cells by excluding aggregates and debris.

Discussion

Cellular arrest was measured by flow cytometry after permeating propidium iodide (PI) into the A375 cells for DNA staining. All cells treated with compositions and controls were predominantly in the $G_0/G_1$ phase and partially in the S-phase (as shown in FIG. 6). The therapeutic agents dissolved in DMSO showed the highest cellular arrest in the $G_0/G_1$ (88% $G_0/G_1$) compared to the DMSO control that experienced cellular arrest in 81% $G_0/G_1$, with the remaining cells in S-phase. The drug/CD and drug/CDgemini compositions arrested the cell cycle in a similar pattern: 66 to 65% $G_0/G_1$ and 34 to 35% S-phase for NC 2067 and 66 to 68% $G_0/G_1$ and 34 to 32% S-phase for NC 2081 respectively. The controls, CD and CDgemini showed cellular arrest in 56 to 65% $G_0/G_1$ and 43 to 35% S-phase, respectively. Little to no cellular arrest was observed in the $G_2/M$ phase.

Figure 7A:
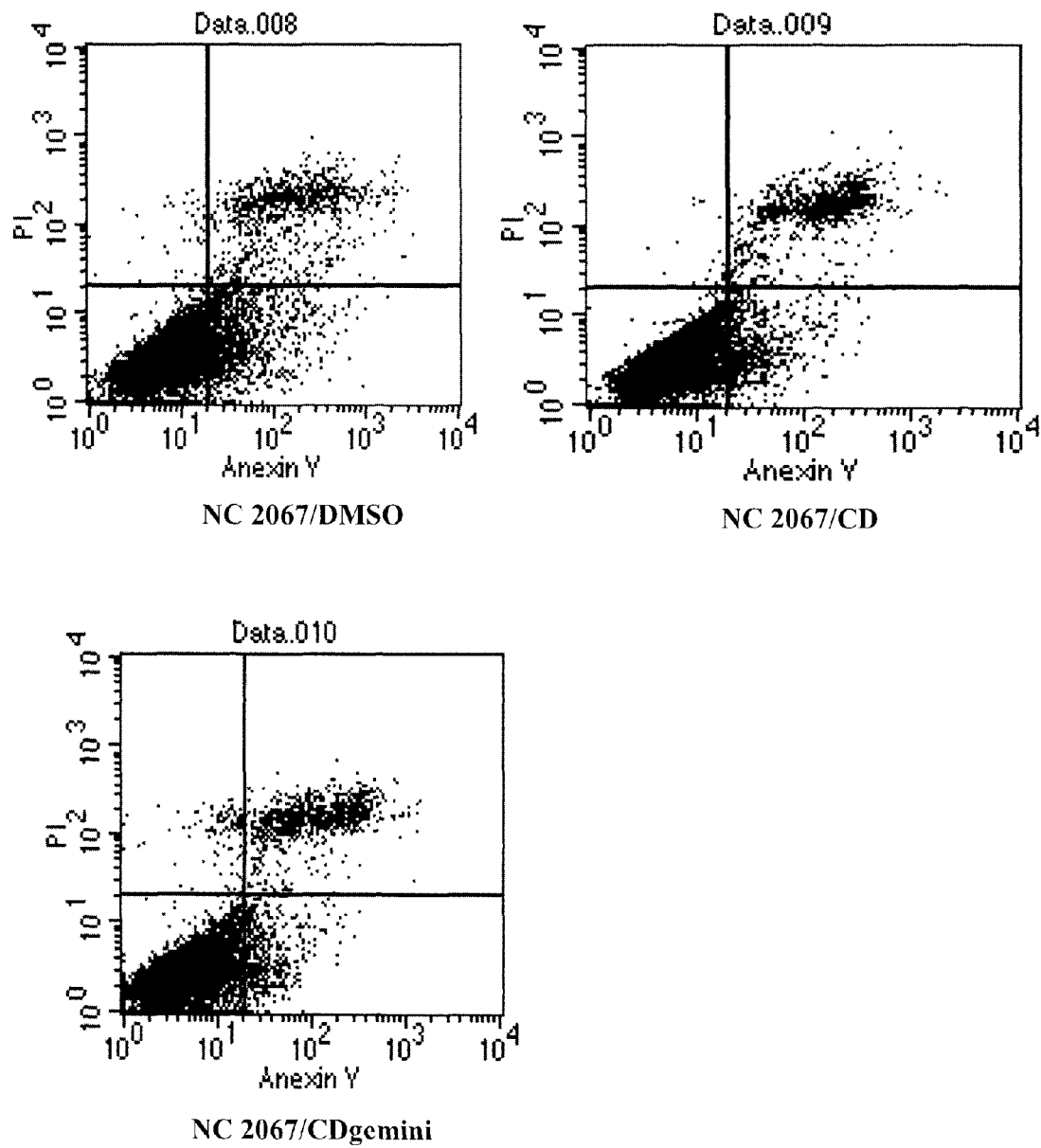
FIG. 7 shows the induction of apoptosis/necrosis in A375 cells treated with compositions of the disclosure and controls as a percentage of total population.
Figure 7B:
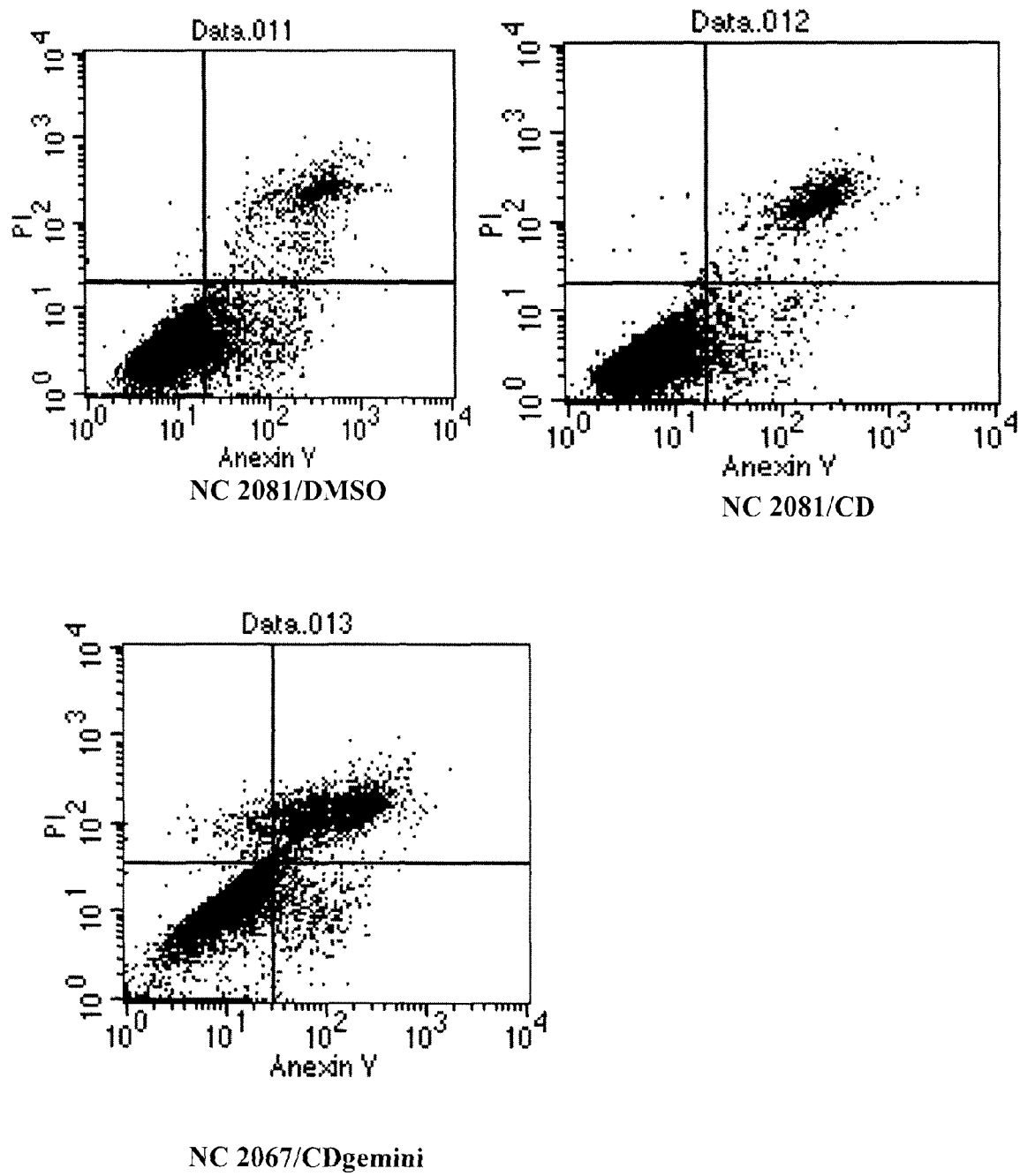
Figure 7C:
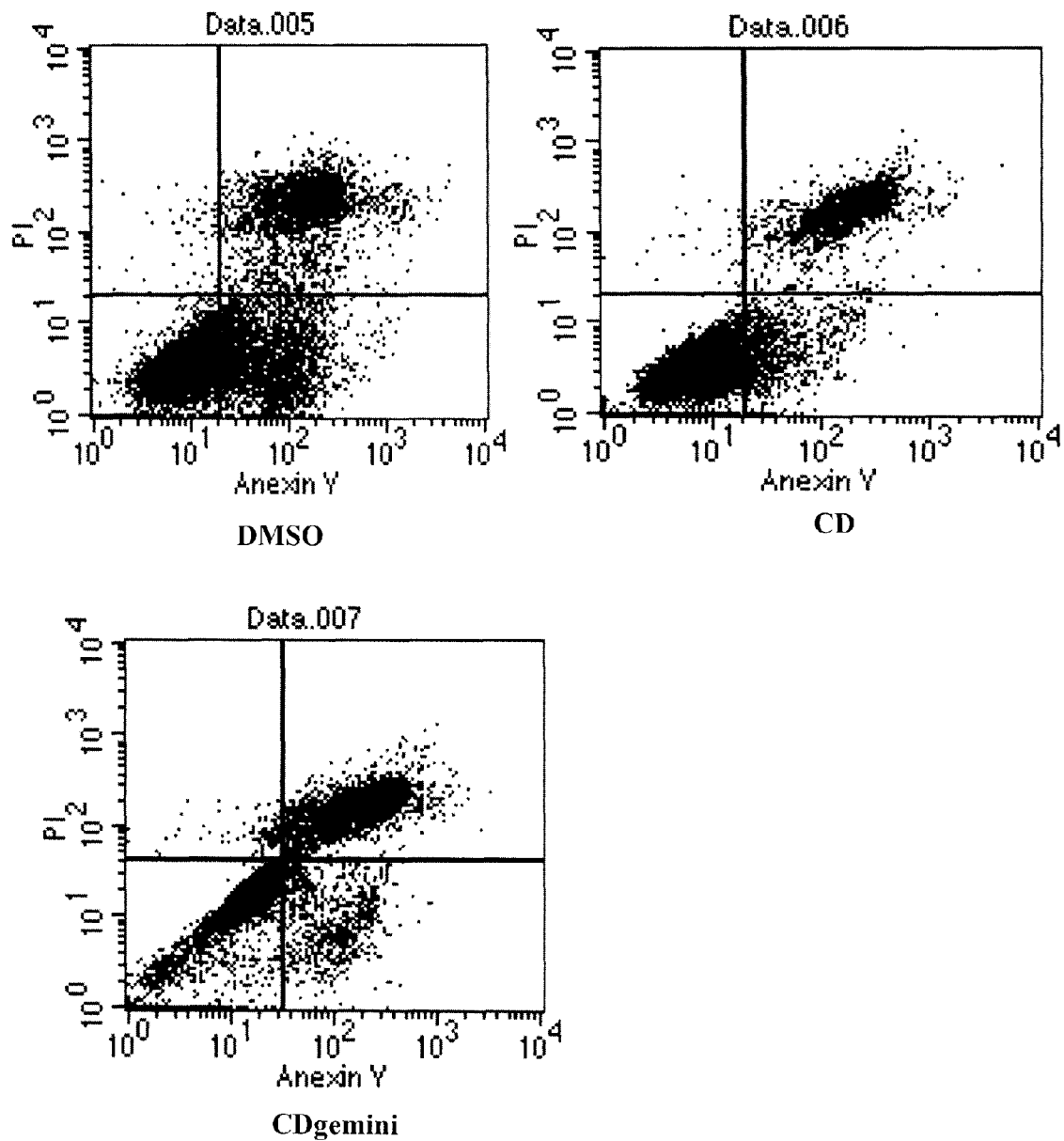

The type of cell death of the A375 cells after treatment of the compositions was captured by performing the apoptosis assay (as shown in FIG. 7). Cells were treated with the therapeutic agents at the $IC_{50}$ concentration of each composition. Apoptosis was measured by dual staining of the cells with Annexin V-FITC and propidium iodide. In apoptotic cells, phosphatidylserine (PS) is translocated from the inner leaflet (cytoplasmic) of the plasma membrane to the outer leaflet (cell surface) without losing the membrane integrity, making it available to strongly bind to Annexin V.[5] The cell membrane in necrotic cells is compromised; thus the propidium iodide can penetrate freely and stain the DNA in the nucleus. The therapeutic agents dissolved in DMSO induced a rate of apoptosis, which reached 18% for NC 2067 and 19% of the total population for NC 2081 compared to 43% for the DMSO without the agent. The drug/CD and drug/CDgemini formulations produced similar apoptotic profiles with 14 to 11% for NC 2067, 11 to 15% for NC 2081 compared to 25 to 31% for the controls, respectively. Necrosis occurred in less than 2% of the total population of cells.

TABLE 1

Size and ζ-potential measurements

| Formulation | Particle size | | | | PDI | ζ potential (mV) |
| --- | --- | --- | --- | --- | --- | --- |
| | Peak 1 (nm) | Intensity (%) | Peak 2 (nm) | Intensity (%) | | |
| CDgemini | 153.6 ± 4.3 | 100 | | | 0.2 | 5.7 ± 0.5 |
| NC 2067/ CDgemini | 173.2 ± 24 | 52-62 | 606.7 ± 39 | 38-48 | <0.5 | 42.5 ± 1.9* |

TABLE 1-continued

Size and ζ-potential measurements

| Formulation | Particle size | | | | PDI | ζ potential (mV) |
|---|---|---|---|---|---|---|
| | Peak 1 (nm) | Intensity (%) | Peak 2 (nm) | Intensity (%) | | |
| NC 2081/ CDgemini | 185.0 ± 17.5 | 96-98.5 | | | 0.3 | 5.1 ± 3.9 |

*Due to the bimodal size distribution, the ζ-potential count rate varied significantly and the zeta potential was trending by 6.8%.

TABLE 2

$IC_{50}$ values of different drug compositions on the human melanoma cell line (A375). The ±value is the standard deviation of triplicate assays.

| Drug/Drug delivery | DMSO (μM) | CD (μM) | CDgemini (μM) |
|---|---|---|---|
| NC 2067 | 0.47 ± 0.03 | 0.80 ± 0.06 | 0.86 ± 0.07 |
| NC 2081 | 0.93 ± 0.03 | 7.0 ± 2.0 | 7.2 ± 2.4 |

REFERENCES CITED HEREIN

1. Vetvicka D, Hruby M, Hovorka O, et al. Biological evaluation of polymeric micelles with covalently bound doxorubicin. Bioconjug Chem 2009; 20:2090-7.
2. Liang X J, Chen C, Zhao Y, Wang P C. Circumventing tumor resistance to chemotherapy by nanotechnology. Methods Mol Biol 2010; 596:467-88.
3. Padsis J, Turley R, Tyler D. Pharmacotherapy of regional melanoma therapy. Expert Opin Pharmacother 2010; 11:79-93.
4. Das U, Alcorn J, Shrivastav A, et al. Design, synthesis and cytotoxic properties of novel 1-[4-(2-alkylaminoethoxy) phenylcarbonyl]-3,5-bis(arylidene)-4-piperidones and related compounds. Eur J Med Chem 2007; 42:71-80.
5. Rosenzweig H S, Rakhmanova V A, MacDonald R C. Diquaternary ammonium compounds as transfection agents. Bioconjug Chem 2001; 12:258-63.
6. Huang J B, Yu D F, Huang X, et al. Effects of inorganic and organic salts on aggregation behavior of cationic gemini surfactants. Journal of Physical Chemistry B 2010; 114: 14955-64.
7. Du X, Chen X, Lu W, Hou J. Spectroscopic study on binding behaviors of different structural nonionic surfactants to cyclodextrins. J Colloid Interface Sci 2004; 274: 645-51.
8. Challa R, Ahuja A, Ali J, Khar R K. Cyclodextrins in drug delivery: An updated review. AAPS PharmSciTech 2005; 6:E329-57.
9. Subramaniam D, May R, Sureban S M, Lee K B, George R, Kuppusamy P, et al. Diphenyl difluoroketone: A curcumin derivative with potent in vivo anticancer activity. Cancer Research 2008 Mar. 15; 68(6):1962-1969.
10. Thomas S L, Zhong D, Zhou W, Malik S, Liotta D, Snyder J P, et al. EF24, a novel curcumin analog, disrupts the microtubule cytoskeleton and inhibits HIF-1. Cell Cycle 2008 August; 7(15):2409-2417.
11. Tan X, Sidell N, Mancini A, Huang R P, Shenming W, Horowitz I R, et al. Multiple anticancer activities of EF24, a novel curcumin analog, on human ovarian carcinoma cells. Reprod Sci 2010 October; 17(10):931-940.
12. Tantishaiyakul V, Wiwattanawongsa K, Pinsuwan S, et al. Characterization of mefenamic acid-guaiacol ester: Stability and transport across caco-2 cell monolayers. Pharm Res 2002; 19:1013-8.
13. Yadav V R, Prasad S, Kannappan R, et al. Cyclodextrin-complexed curcumin exhibits anti-inflammatory and anti-proliferative activities superior to those of curcumin through higher cellular uptake. Biochem Pharmacol 2010; 80:1021-32.
14. Dreaden E C, Mwakwari S C, Sodji Q H, Oyelere A K, El-Sayed M A. Tamoxifen-poly(ethylene glycol)-thiol gold nanoparticle conjugates: Enhanced potency and selective delivery for breast cancer treatment. Bioconjug Chem 2009; 20:2247-53.
15. Hu C M, Zhang L. Therapeutic nanoparticles to combat cancer drug resistance. Curr Drug Metab 2009; 10:836-41.
16. Bush J A, Cheung K J, Jr., Li G. Curcumin induces apoptosis in human melanoma cells through a fas receptor/caspase-8 pathway independent of p53. Exp Cell Res 2001; 271:305-14.
17. Turley R S, Raymond A K, Tyler D S. Regional treatment strategies for in-transit melanoma metastasis. Surg Oncol Clin N Am 2011; 20:79-103.
18. Mittal S, Song X, Vig B S, Amidon G L. Proline prodrug of melphalan targeted to prolidase, a prodrug activating enzyme overexpressed in melanoma. Pharm Res 2007; 24:1290-8.

The invention claimed is:

1. A pharmaceutical composition comprising a drug delivery agent and a therapeutic agent, wherein the drug delivery agent comprises a compound of the formula (I):

CD-L-G    (I)

wherein,
CD is a cyclodextrin;
L is a linker moiety; and
G is a gemini surfactant.

2. The pharmaceutical composition according to claim 1, wherein the linker moiety L is $(C_1\text{-}C_{20})$-alkylene, $(C_2\text{-}C_{20})$-alkenylene, $(C_2\text{-}C_{20})$-alkynylene, $(C_3\text{-}C_{10})$-cycloalkylene, or any combination thereof, wherein said 4 groups are optionally substituted by one or more groups selected from halo, (=O), $OR^1$ or $R^1$, in which $R^1$ is selected from $(C_1\text{-}C_6)$-alkyl, $(C_2\text{-}C_6)$-alkenyl, $(C_2\text{-}C_6)$-alkynyl or $(C_3\text{-}C_6)$-cycloalkyl, and wherein one or more carbon atoms in said 4 groups is optionally replaced with a heteromoiety selected from O, S, N, NH or $N(C_1\text{-}C_6)$-alkyl.

3. The pharmaceutical composition according to claim 2, wherein the linker moiety L is $(C_1\text{-}C_{10})$-alkylene, $(C_2\text{-}C_{10})$-alkenylene, $(C_2\text{-}C_{10})$-alkynylene, $(C_3\text{-}C_8)$-cycloalkylene, or any combination thereof.

4. The pharmaceutical composition according to claim 3, wherein the linker moiety L is

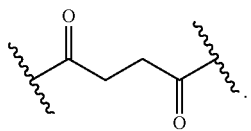 [SMILES: *C(=O)CCC(*)=O]

5. The pharmaceutical composition according to claim 1, wherein the moiety of the gemini surfactant G is a moiety of the formula (II):

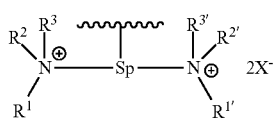

wherein $R^1$ and $R^{1'}$ are independently or simultaneously $(C_5-C_{30})$-alkyl, $(C_5-C_{30})$-alkenyl, $(C_5-C_{30})$-alkynyl or $(C_6-C_{16})$-aryl, all 3 groups optionally substituted by one or more groups selected from halo, $OR^4$ or $R^4$, in which $R^4$ is selected from $(C_1-C_6)$-alkyl, $(C_2-C_6)$-alkenyl, $(C_2-C_6)$-alkynyl or $(C_3-C_6)$-cycloalkyl, and wherein one or more carbon atoms in said 3 groups is optionally replaced with a heteromoiety selected from O, S, N, NH or N($C_1-C_6$)-alkyl;

$R^2$, $R^3$, $R^{2'}$ and $R^{3'}$ are independently $(C_1-C_{10})$-alkyl, $(C_2-C_{10})$-alkenyl or $(C_2-C_{10})$-alkynyl all 3 groups optionally substituted by one or more groups selected from halo, $OR^5$ or $R^5$, in which $R^5$ is selected from $(C_1-C_6)$-alkyl, $(C_2-C_6)$-alkenyl, $(C_2-C_6)$-alkynyl or $(C_3-C_6)$-cycloalkyl;

Sp is a spacer moiety bonded to the linker moiety L; and

X is any suitable anionic counterion.

6. The pharmaceutical composition according to claim 5, wherein $R^1$ and $R^{1'}$ are independently or simultaneously $(C_{10}-C_{22})$-alkyl, $(C_{10}-C_{22})$-alkenyl, $(C_{10}-C_{22})$-alkynyl or $(C_6-C_{10})$-aryl.

7. The pharmaceutical composition according to claim 5, wherein $R^2$, $R^3$, $R^{2'}$ and $R^{3'}$ are independently or simultaneously methyl, ethyl, propyl or iso-propyl.

8. The pharmaceutical composition according to claim 5, wherein the spacer moiety Sp is $(C_1-C_{10})$-alkylene, $(C_2-C_{20})$-alkenylene, $(C_2-C_{20}$-alkynylene, $(C_3-C_{10})$-cycloalkylene, or any combination thereof, wherein said 4 groups are optionally substituted by one or more groups selected from halo, $OR^5$ or $R^5$, in which $R^5$ is selected from $(C_1-C_6)$-alkyl, $(C_2-C_6)$-alkenyl, $(C_2-C_6)$-alkynyl or $(C_3-C_6)$-cycloalkyl, and wherein one or more carbon atoms in said 4 groups is optionally replaced with a heteromoiety selected from O, S, N, NH or N($C_1-C_6$)-alkyl.

9. The pharmaceutical composition according to claim 8, wherein the spacer moiety Sp is $(C_1-C_{10})$-alkylene, $(C_2-C_{10})$-alkenylene, $(C_2-C_{10}$-alkynylene, $(C_3-C_6)$-cycloalkylene, or any combination thereof.

10. The pharmaceutical composition according to claim 9, wherein the spacer moiety Sp is $(C_1-C_8)$-alkylene, wherein one or more carbon atoms in said group is optionally replaced with a heteromoiety selected from O, S, N, NH or N($C_1-C_6$)-alkyl.

11. The pharmaceutical composition according to claim 10, wherein the spacer moiety Sp is

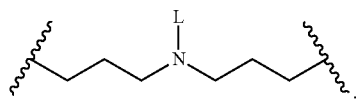

12. The pharmaceutical composition according to claim 5, wherein $X^-$ is a halogen ion.

13. The pharmaceutical composition according to claim 5, wherein gemini surfactant moiety of the formula (II) is

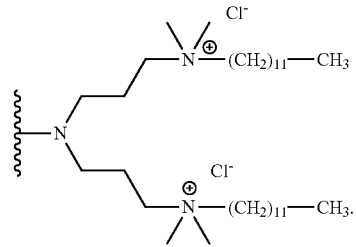

14. The pharmaceutical composition according to claim 1, wherein the cyclodextrin is β-cyclodextrin.

15. The pharmaceutical composition according to claim 1, wherein the compound of formula (I) is

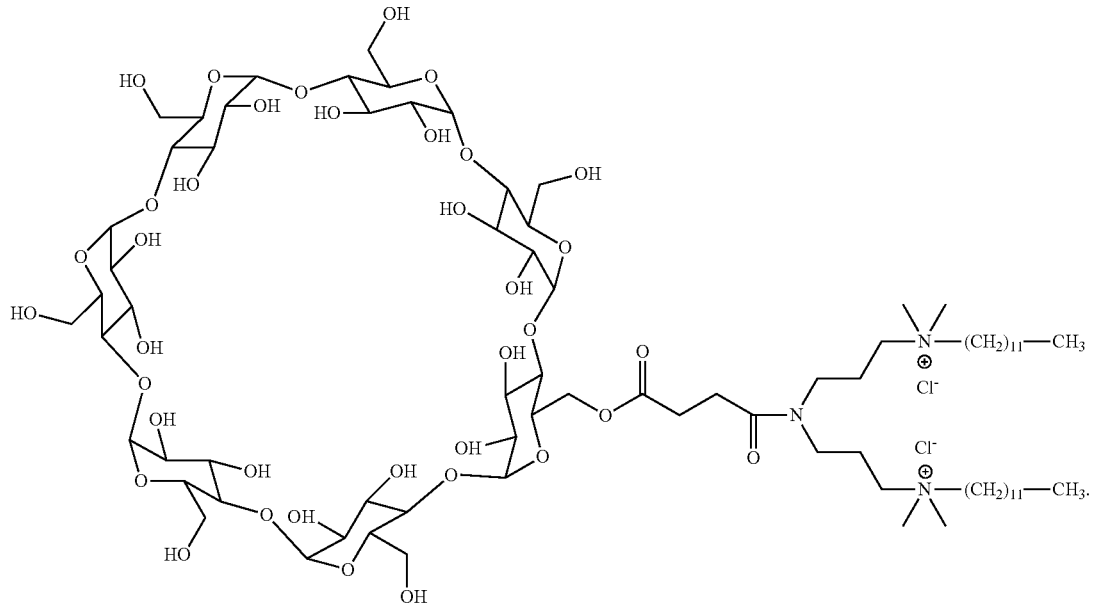

16. The pharmaceutical composition according to claim 1, wherein the therapeutic agent is lipophilic.

17. The pharmaceutical composition according to claim 1, wherein the therapeutic agent comprises an antineoplastic agent.

18. A pharmaceutical delivery agent comprising a compound of the formula (I)

CD-L-G (I)

wherein CD, L and G are as defined in claim 1.

* * * * *